(12) United States Patent
Chisena et al.

(10) Patent No.: US 11,464,949 B2
(45) Date of Patent: Oct. 11, 2022

(54) SYSTEM FOR EFFECTING AND CONTROLLING OSCILLATORY PRESSURE WITHIN BALLOON CATHETERS FOR FATIGUE FRACTURE OF CALCULI

(71) Applicant: THE REGENTS OF THE UNIVERSITY OF MICHIGAN, Ann Arbor, MI (US)

(72) Inventors: Robert Chisena, Ann Arbor, MI (US); Hitinder S. Gurm, Ann Arbor, MI (US); Matthew Hildner, Ann Arbor, MI (US); Yihao Zheng, Ann Arbor, MI (US); Albert Shih, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 113 days.

(21) Appl. No.: 16/654,073

(22) Filed: Oct. 16, 2019

(65) Prior Publication Data

US 2020/0046949 A1 Feb. 13, 2020

Related U.S. Application Data

(63) Continuation-in-part of application No. PCT/US2019/027139, filed on Apr. 12, 2019.
(Continued)

(51) Int. Cl.
*A61M 25/10* (2013.01)
*A61B 17/22* (2006.01)
*A61B 17/00* (2006.01)

(52) U.S. Cl.
CPC . *A61M 25/10182* (2013.11); *A61B 17/22012* (2013.01); *A61M 25/10185* (2013.11);
(Continued)

(58) Field of Classification Search
CPC ...... A61M 25/10182; A61M 25/10185; A61M 2205/3344; A61M 25/10187;
(Continued)

(56) References Cited

U.S. PATENT DOCUMENTS 2,918,917 A 12/1959 Emerson
4,446,867 A 5/1984 Leveen et al.
(Continued)

FOREIGN PATENT DOCUMENTS

CA 2651380 C 5/2015
DE 19936162 A1 2/2001
(Continued)

OTHER PUBLICATIONS

International Search Report and Written Opinion regarding International Application No. PCT/US2020/055458, dated Feb. 8, 2021.
(Continued)

*Primary Examiner* — Julian W Woo
(74) *Attorney, Agent, or Firm* — Harness, Dickey & Pierce, P.L.C.

(57) ABSTRACT

A dynamic balloon angioplasty system for applying a dynamic pressure to fracture hardened materials embedded within an elastic conduit. The system having a pressure source system outputting at least a first predetermined pressure from a pressure source outlet, and an angioplasty unit fluidly coupled to the pressure source outlet receiving at least the first predetermined pressure. The angioplasty unit having an angioplasty inflation device, an angioplasty balloon connector, and an oscillating mechanism selectively actuated to output a plurality of pressure pulses to the angioplasty balloon via a fluid communication path. A control system is configured to determine an optimal hydraulic pressure oscillation frequency and amplitude for a given procedure and output a control signal to the oscillating
(Continued)

mechanism, and monitor a pressure signal to detect fracture of the hardened material within the elastic conduit or system failure or leakage.

39 Claims, 18 Drawing Sheets

Related U.S. Application Data

(60) Provisional application No. 62/656,699, filed on Apr. 12, 2018.

(52) U.S. Cl.
CPC ........... *A61B 2017/00154* (2013.01); *A61B 2017/00181* (2013.01); *A61B 2017/00539* (2013.01); *A61B 2017/22001* (2013.01); *A61B 2017/22051* (2013.01); *A61B 2017/22062* (2013.01); *A61M 2205/3344* (2013.01)

(58) Field of Classification Search
CPC ....... A61M 25/10184; A61B 17/22012; A61B 2017/00154; A61B 2017/00539; A61B 2017/00181; A61B 2017/22051; A61B 2017/22001; A61B 2017/22062; A61B 2017/00194; A61B 2017/00185; A61B 2017/00132; A61B 2017/00548; A61B 2017/00017; A61B 2017/22014
See application file for complete search history.

(56) References Cited

U.S. PATENT DOCUMENTS

| | | | |
|---|---|---|---|
| 4,936,281 A | 6/1990 | Stasz | |
| 5,021,046 A * | 6/1991 | Wallace | A61M 25/104 604/97.03 |
| 5,215,523 A | 6/1993 | Williams et al. | |
| 5,308,356 A | 5/1994 | Blackshear, Jr. et al. | |
| 5,318,533 A | 6/1994 | Adams et al. | |
| 5,344,395 A | 9/1994 | Whalen et al. | |
| 5,407,424 A | 4/1995 | LaFontaine et al. | |
| 5,460,609 A | 10/1995 | O'Donnell | |
| 5,545,133 A * | 8/1996 | Burns | A61M 25/10187 604/99.04 |
| 5,599,301 A | 2/1997 | Jacobs et al. | |
| 5,609,606 A | 3/1997 | O'Boyle | |
| 5,611,807 A | 3/1997 | O'Boyle | |
| 5,722,979 A | 3/1998 | Kusleika | |
| 5,846,218 A | 12/1998 | Brisken et al. | |
| 5,891,089 A * | 4/1999 | Katz | A61M 25/104 604/97.01 |
| 5,944,687 A | 8/1999 | Benett et al. | |
| 6,176,235 B1 | 1/2001 | Benarrouch et al. | |
| 6,179,815 B1 | 1/2001 | Foote | |
| 6,354,999 B1 | 3/2002 | Dgany et al. | |
| 6,544,224 B1 | 4/2003 | Steese-Bradley | |
| 7,166,098 B1 | 1/2007 | Steward et al. | |
| 7,604,618 B2 | 10/2009 | Dixon et al. | |
| 7,942,850 B2 * | 5/2011 | Levit | A61M 25/10188 604/103.07 |
| 7,981,078 B2 * | 7/2011 | Mandel | A61M 25/10188 604/100.03 |
| 7,998,107 B2 * | 8/2011 | Nash | A61M 1/743 604/35 |
| 8,147,511 B2 | 4/2012 | Perry et al. | |
| 8,197,505 B2 | 6/2012 | Hirszowicz et al. | |
| 8,372,034 B2 | 2/2013 | Levit et al. | |
| 8,574,248 B2 | 11/2013 | Kassab | |
| 8,628,555 B2 | 1/2014 | Perry et al. | |
| 8,728,091 B2 | 5/2014 | Hakala et al. | |
| 8,747,416 B2 | 6/2014 | Hakala et al. | |
| 8,808,237 B2 | 8/2014 | Thielen et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 9,011,462 B2 | 4/2015 | Adams et al. | |
| 9,072,534 B2 | 7/2015 | Adams et al. | |
| 9,138,249 B2 | 9/2015 | Adams et al. | |
| 9,333,000 B2 | 5/2016 | Hakala et al. | |
| 9,375,223 B2 | 6/2016 | Wallace | |
| 9,433,428 B2 | 9/2016 | Hakala et al. | |
| 9,468,745 B2 | 10/2016 | Bagaoisan et al. | |
| 9,642,673 B2 | 5/2017 | Adams et al. | |
| 2002/0045854 A1 | 4/2002 | Royo et al. | |
| 2004/0199230 A1 | 10/2004 | Yon | |
| 2007/0088380 A1 | 4/2007 | Hirszowicz et al. | |
| 2008/0140101 A1 | 6/2008 | Carley et al. | |
| 2009/0171278 A1 | 7/2009 | Hirszowicz et al. | |
| 2009/0247945 A1 | 10/2009 | Levit et al. | |
| 2011/0196412 A1 | 8/2011 | Levit et al. | |
| 2012/0253186 A1 | 10/2012 | Simpson et al. | |
| 2021/0100570 A1 * | 4/2021 | Schoenle | A61M 25/10182 |

FOREIGN PATENT DOCUMENTS

| | | |
|---|---|---|
| EP | 0870484 A1 | 10/1998 |
| JP | 2011528963 A | 12/2011 |
| WO | 200110491 A2 | 2/2001 |
| WO | 2009141810 A2 | 11/2009 |
| WO | 2012006625 A2 | 1/2012 |
| WO | 2019200201 A1 | 10/2019 |

OTHER PUBLICATIONS

"Comparison of Slow Oscillating Versus Fast Balloon Inflation Strategies for Coronary Angioplasty," Blankenship, James C., Mitchell W. Krucoff, Steven W. Wems, H. Vernon Anderson, Charles Landau, Harvey J. White, Cindy L. Green, Artur M. Spokojny, Richard G. Bach, Russell E. Raymond, Jackie Pinkston, Millie Rawert, and J. David Talley, The American Journal of Cardiology, vol. 83, Mar. 1, 1991.

"Coronary Dissection Resulting From Angioplasty With Slow Oscillating vs. Rapid Inflation and Slow vs. Rapid Deflation," Blankenship, James C., Alan C. Ford, Sheldon D. Henry, Carolin M. Frey, Catherization and Caridovascular Diagnosis 34:202-209 (1995).

"Oscillating Balloon Angioplasty: Does Pressure Oscillation Reach the Balloon?," Blankenship, James C., Duc Nguyen, and Laksen Sirimanne, Catherization and Caridovascular Diagnosis 37:109-112, (1996).

International Preliminary Report on Patentability regarding International Application No. PCT/US2020/055458, dated Oct. 16, 2019.

* cited by examiner $f_2 > f_1$, but base pressure within evacuated pressure range

SYSTEM FOR EFFECTING AND CONTROLLING OSCILLATORY PRESSURE WITHIN BALLOON CATHETERS FOR FATIGUE FRACTURE OF CALCULI

CROSS-REFERENCE TO RELATED APPLICATIONS

This application is a continuation-in-part of International Application No. PCT/US2019/027139, filed on Apr. 12, 2019, which claims the benefit of U.S. Provisional Application No. 62/656,699, filed on Apr. 12, 2018. The entire disclosures of the above applications are incorporated herein by reference.

FIELD

The present disclosure relates to a method, apparatus, and control mechanism for creating pressure oscillations with large, controllable amplitudes and high frequencies in a balloon-based medical device. Embodiments of this apparatus relate to automated and controlled methods of creating hydraulic-pressure oscillations to perform tasks such as, for example, fracturing hardened materials embedded within elastic conduits. The overall system may be used, for example, for multiple medical applications including, but not limited to, treatment of cardiovascular atherosclerosis, treatment of calcified valves, or a genitourinary device for the treatment of genitourinary calculi. However, the embodiments described herein are not solely limited to these fields and uses.

BACKGROUND AND SUMMARY

This section provides background information related to the present disclosure which is not necessarily prior art. This section also provides a general summary of the disclosure and is not a comprehensive disclosure of its full scope or all of its features.

Ischemic heart disease, the number one cause of death in the world, is caused by atherosclerotic plaque build-up within human vasculature. Worldwide, these diseases represent 84.5% of cardiovascular deaths and 28.2% of overall mortality. Ischemic heart disease is developed through a mechanism called atherosclerosis, which is the accumulation of fatty and calcified materials that cause stenosis, the narrowing of the arterial lumen. Both the coronary and peripheral arteries may suffer from atherosclerotic plaque accumulation.

Balloon angioplasty with stenting is a common treatment for stenoses caused by atherosclerotic lesions in coronary and peripheral artery diseases. The mechanical properties of a specific lesion found in a patient can vary widely, ranging from soft, lipid-core atheromatous plaques to hard, calcified structures. The calcified structures or calcified lesions have proven to be particularly challenging to treat. The common treatment of balloon angioplasty employs a pressurized catheter balloon to fracture atherosclerotic plaques and expand them into artery walls to re-establish normal blood flow in stenosed arteries. Typically, the balloon is pressurized via a manually actuated screw-driven syringe, which converts rotations of a physician-facing handle into a displacement of the syringe piston. The handle of the syringe is rotated by a clinician until the pressure within the system reaches a desired pressure, or the physician senses fracture of the calcified plaque.

During angioplasty, the physician can sense if the calcified plaque has fractured in two ways: (1) from the outline of the balloon under fluoroscopy, a medical imaging technique commonly used in cardiovascular procedures, and (2) from a reduction in pressure within the hydraulic system as indicated by a pressure gauge. During angioplasty procedures, a radiopaque dye is introduced into the balloon, which under fluoroscopy, illuminating the outline of the balloon and arterial walls. When the plaque is intact and the balloon is pressurized, the balloon assumes a characteristic dog-bone shape in which the proximal and distal edges are unrestricted to expand but the middle is obstructed by the plaque. The shape of the dog-bone informs the clinician of the severity and distribution of the plaque. A more uniformly expanded balloon indicates to the physician that the plaque has been treated. The second method used to sense plaque fracture is indicated by the pressure gauge attached to the balloon. When treating severe and/or circumferentially distributed plaque, pressure is increased in the balloon until the plaque fractures. Prior to fracture of the plaque, the balloon maintains the previously described dog-bone shape. Upon fracture, the plaque no longer restricts the balloon expansion, and the balloon expands the plaque into the elastic artery. With this balloon expansion, the volume of the balloon increases, transforming it from a dog-bone shape into a fully expanded cylindrical shape. This volume increase causes the pressure in the balloon to drop, a change that may be visualized or sensed from the connected pressure gauge.

Balloon angioplasty of cases with severely calcified plaque often requires high balloon pressure, often exceeding 20 atm (atmospheric pressure). These high pressures apply large stresses to the patient's blood vessels. Physicians often must weigh the risk of increasing balloon pressure, which may cause vessel dissection, a significant adverse event, with leaving the plaque untreated. Even with high pressures in conventional balloon angioplasty, the balloon may fail to sufficiently expand and prepare the lesion for stent placement.

Improving treatment of calcified plaque requires an understanding of its susceptible fracture mechanisms. FIG. 1 shows an experimentally-measured stress-strain and fracture mechanism of calcified plaque. In this measurement, calcified plaque is subjected to a 3-point bend test, and the stress and strain in the plaque is measured during loading. As shown, the calcified plaque has an elastic-deformation zone and a plastic-deformation zone. When the calcified plaque is loaded to any stress in the plastic deformation zone, permanent deformation of the structure through crack growth occurs. When the calcified plaque is loaded to the rupture stress, the calcified plaque completely ruptures. However, to achieve rupture, high stresses in the calcified plaque are required, which leads to surrounding vessel injury. This injury occurs frequently during the conventional static balloon angioplasty process because balloon pressures must induce stresses large enough in the calcified plaque to achieve rupture. However, to minimize damage to the surrounding tissue, the calcified plaque can be fractured at lower pressure through a process known as cyclical loading. In this cyclical loading, the calcified plaque is subjected to an oscillatory stress with a peak stress in the plastic deformation zone. With these cyclical loading conditions, the irregular surface and interior of calcified plaque, which contain many microcracks and pits exhibiting stress concentrations during loading, progressively and permanently grow and deform. With the repeated loading and unloading, the microcracks, due to local stress concentrations, grow, propagate, and induce fracture of the plaque. Therefore, there exists a need for a change in practice from conventional, static balloon angioplasty in which the plaque is held solely in tension (and results in vessel injury due to the high pressures required to generate rupture) to dynamic balloon angioplasty in which the plaque is repeatedly loaded using an oscillating balloon to promote microcrack propagation and induce plaque fracture at a stress significantly lower than the initial plaque structural strength.

A system is prescribed in various embodiments to methods, devices, and systems for fracturing hardened materials embedded within an elastic conduit. For all embodiments presented, the present disclosure describes applications related to treating atherosclerotic calcifications within an arterial conduit, such as a coronary or peripheral artery. However, the present system and teachings are not solely limited to atherosclerotic calcifications nor arterial conduits and may be generally applied to other applications as determined by those skilled in the art.

Generally, the various embodiments described herein enable dynamic balloon angioplasty (DBA), a technique that uses pressure oscillations with a generalized waveform (in some embodiments, harmonic, or frequency-specific, pressure waveform oscillations) to effectively and safely fracture calcified lesions during angioplasty. The concept of DBA for treating arterial calcified plaque is illustrated in FIGS. 2A-2E. In DBA, a catheter 16 with balloon 2 is deployed to the vessel 300 with calcification 600 (FIG. 2B). Through the angioplasty balloon, the plaque is subjected to high-frequency pressure oscillations (FIGS. 2C-2D). In the low-pressure phase of the oscillations (FIG. 2C), the balloon pressure is reduced to near the minimum pressure needed to achieve balloon inflation, typically 1-2 atm. In the high-pressure phase of the oscillations (FIG. 2D), the balloon is inflated to a peak pressure, set by the physician. Typical peak inflation pressures may be from above the low-pressure range to the balloons' max rated pressure, which could be 25 atm or more. Pressure cycling of the balloon in this manner induces cyclic loading of the calcified plaque 600 below the calcified plaque's rupture stress yet in the plastic deformation zone. Calcified plaque 600 from a human femoral artery is shown in FIG. 3A. A high-resolution computed tomography scan of the calcified plaque of FIG. 3A, shown in FIG. 3B, demonstrates a highly irregular interior and surface. The heterogeneity of the calcified plaque interior is composed of many microfractures with sharp corners. Through the fracture mechanisms described herein, the cyclic loading described in FIG. 2 causes cyclic stresses at these sharp corners near plaque microfractures and irregular surfaces. The cyclic stress initiates and grows these sharp corners, which expand the microfractures into larger macroscopic fractures. The growth of these microfractures leads to the more complete fracture of plaque at lower inflation pressures compared to static pressure. Higher frequency pressure cycles and higher-pressure differences between the cycles is expected to increase the effectiveness of this crack growth mechanism. By generating controlled high-frequency pressures cycles in an angioplasty balloon, DBA is expected to lower the required balloon pressure for fracturing calcified plaque, improve stent deployment, improve and control drug delivery for drug-coated balloons, stress-soften soft, lipid-core atheromatous plaques, expand calcified in-stent restenoses, and fracture calcifications on diseased cardiac valves leaflets and improve balloon-based expansion and deployment of prosthesis and devices.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations. The drawings described herein are not intended to limit the scope of the present disclosure.

Figure 14A:
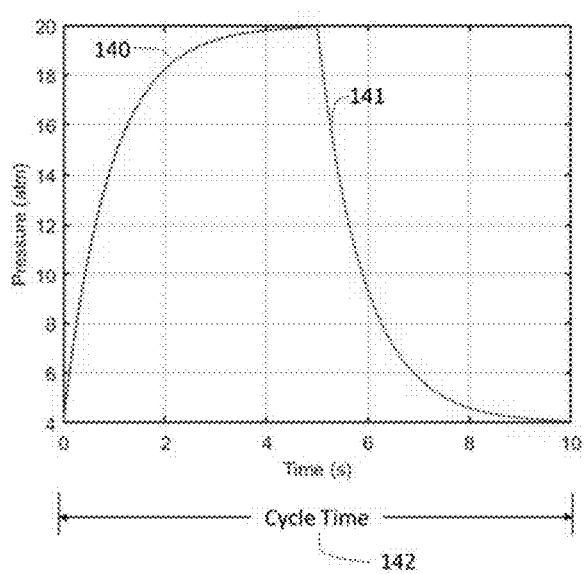
FIG. 14A is a minimum cycle time pressure waveform seen with static balloon angioplasty with a narrow flow channel lumen according to the prior art.
Figure 14B:
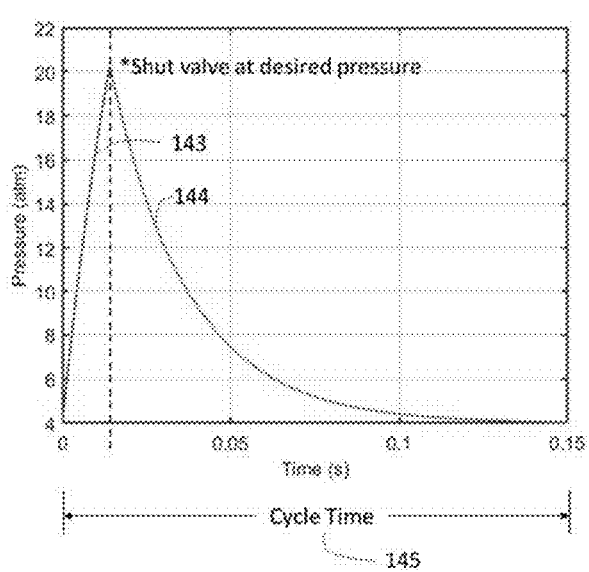
Figure 15:
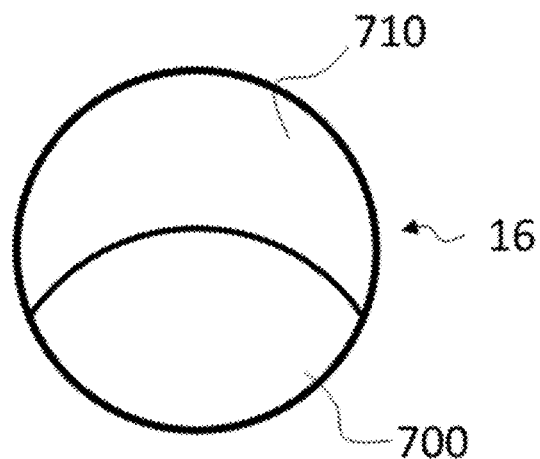

FIG. 14B is a higher frequency pressure waveform seen with expanded flow channel lumen and inlet pressure at 4× desired balloon pressure. To achieve the desired pressure, a control system determines when to shut off the valve and exhaust the system. Additionally, an increased diameter flow channel lumen reduces required pressurization and exhaust cycle times FIG. 15 is a cross-sectional schematic of an angioplasty catheter.

Figure 16:
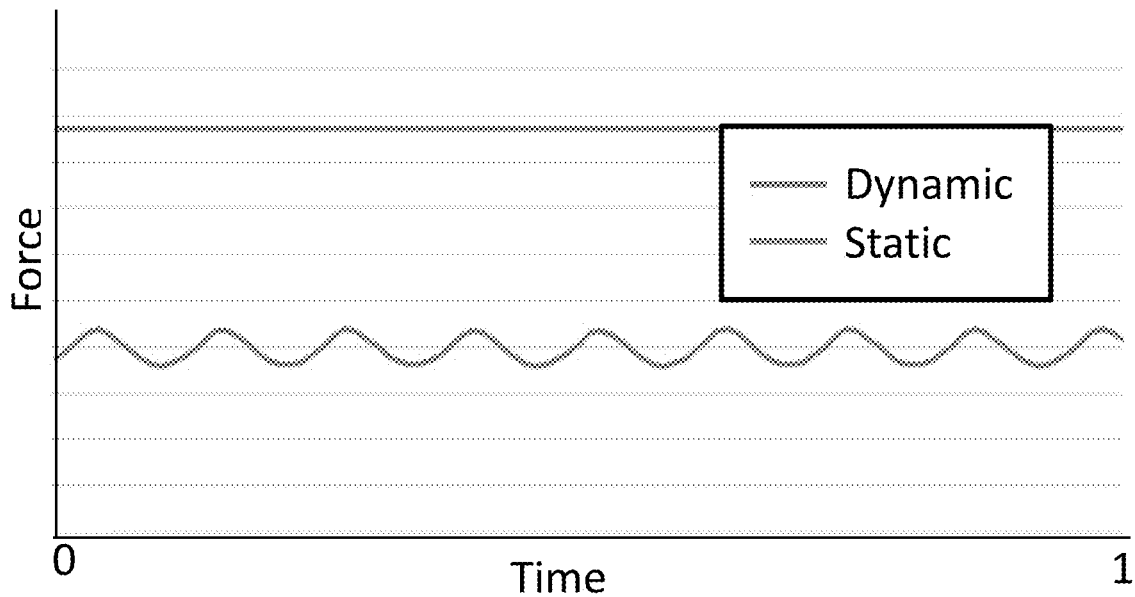

FIG. 16 is the force generated at the balloon from a 10 Hz oscillatory pressure applied to a conventional angioplasty catheter.

Figure 17:
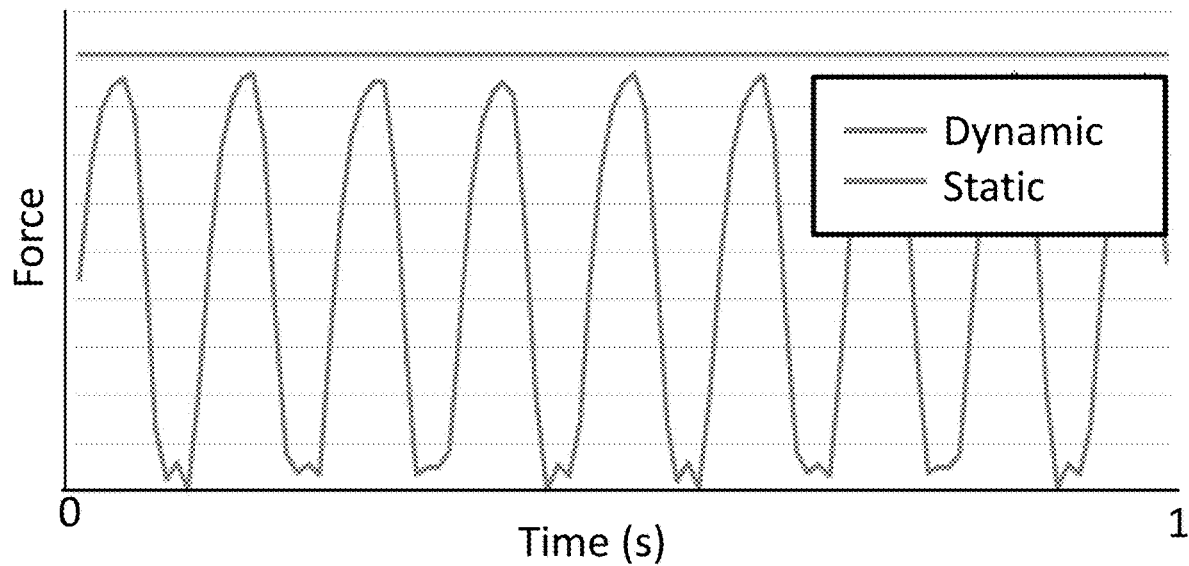

FIG. 17 is the force generated at the balloon with the exemplary angioplasty catheter with expanded flow lumen and braided shaft from a 10 Hz oscillatory pressure.

Figure 18A:
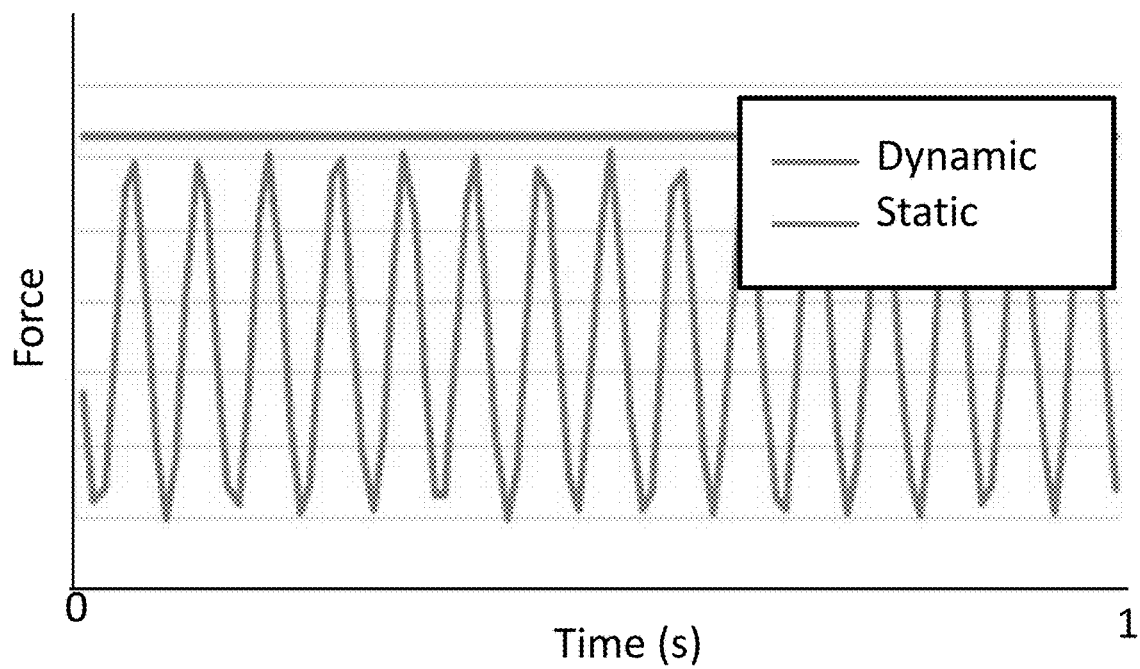
Figure 18B:
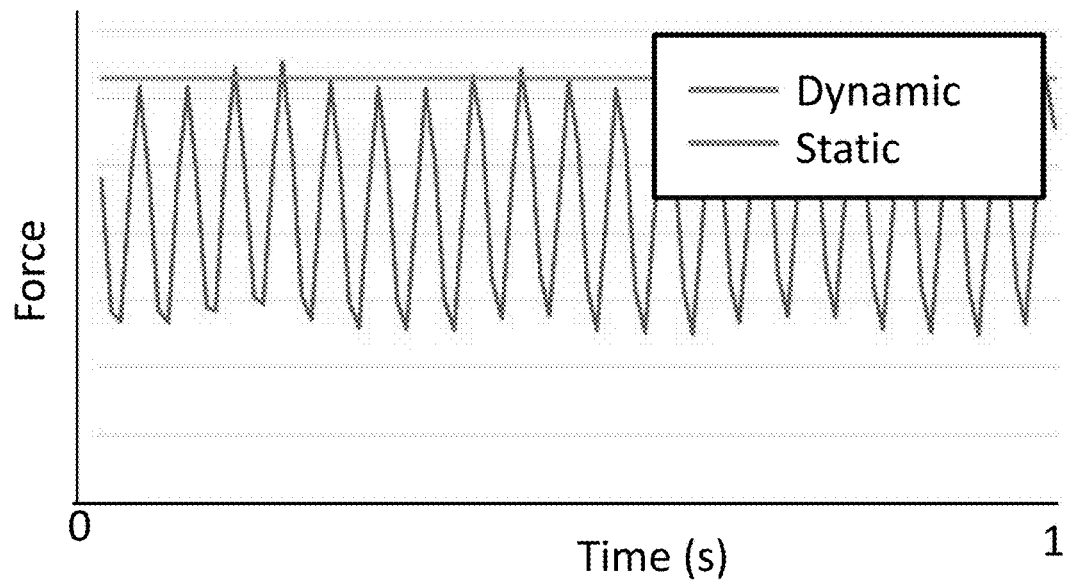

FIGS. 18A and 18B show the force generated at the balloon with the exemplary angioplasty catheter with expanded flow lumen and braided shaft from a 15 Hz and 20 Hz oscillatory pressure, respectively.

Figure 19:
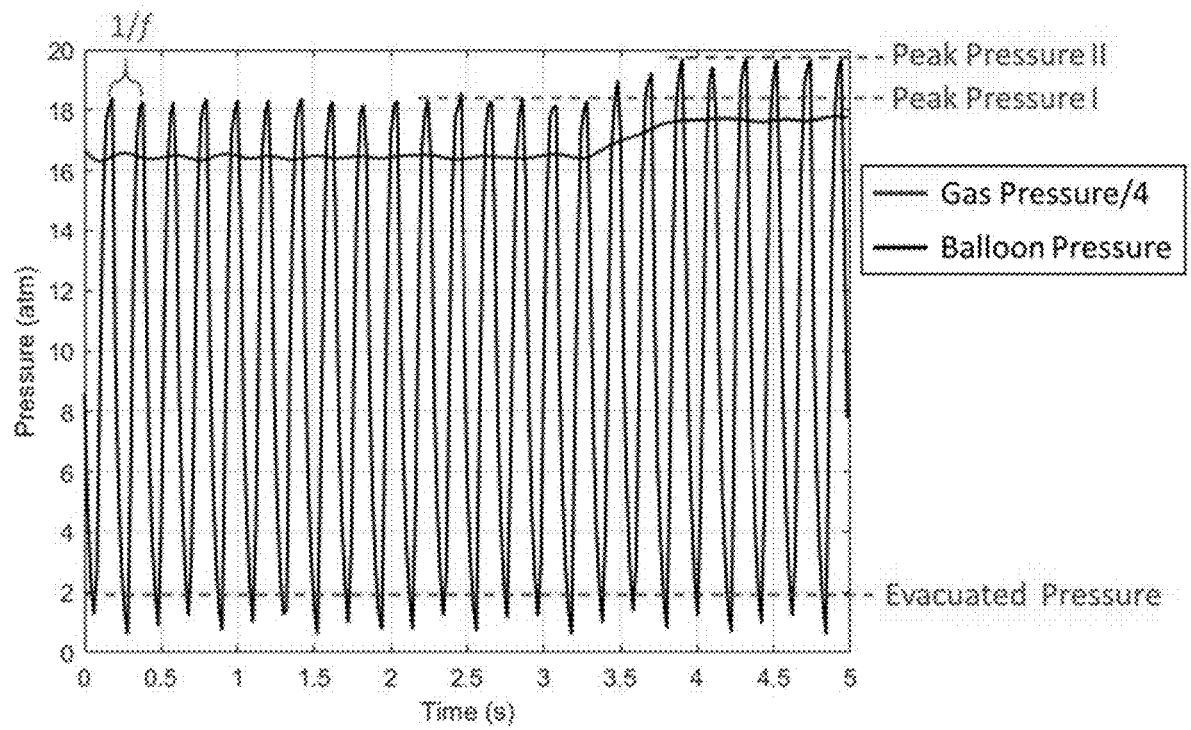

FIG. 19 is an oscillatory balloon pressure waveform in which the balloon is oscillating at a frequency of f and between a peak pressure of 18 atm and an evacuated pressure of 0-2 atm. If desired, the clinician may increase the peak pressure (e.g. from Peak Pressure I to Peak Pressure II). To control the system, the input gas pressure may be compared with the output balloon pressure to adjust system timing.

Figure 20:
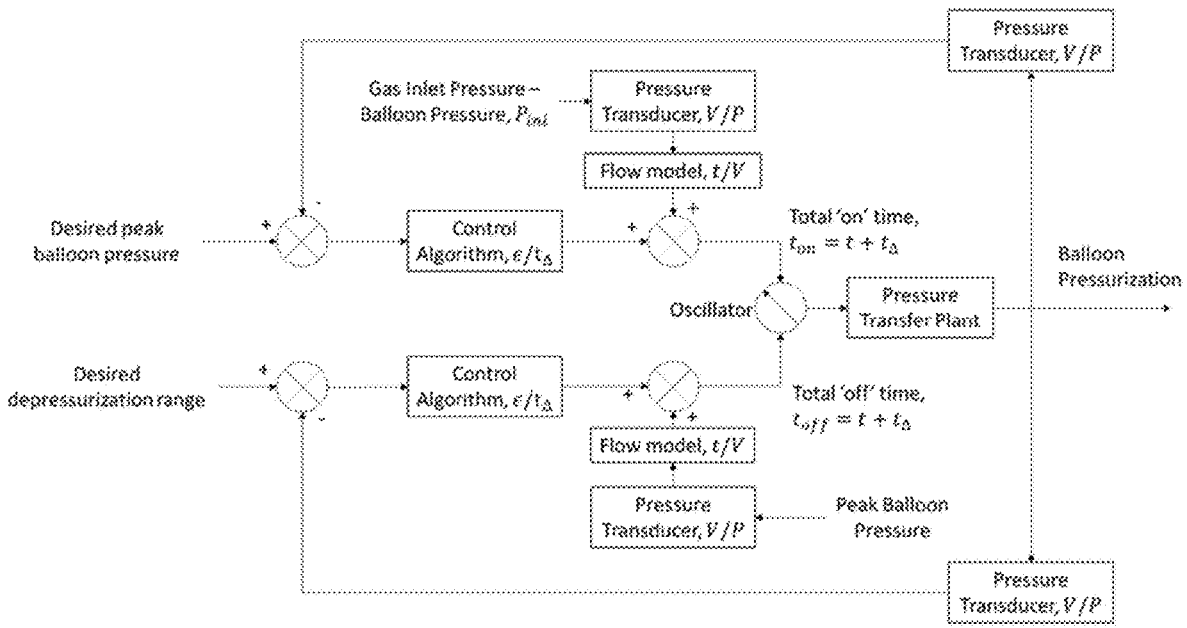

FIG. 20 is a control algorithm flow chart for setting oscillating frequency according to the principles of the present teachings.

Figure 21:
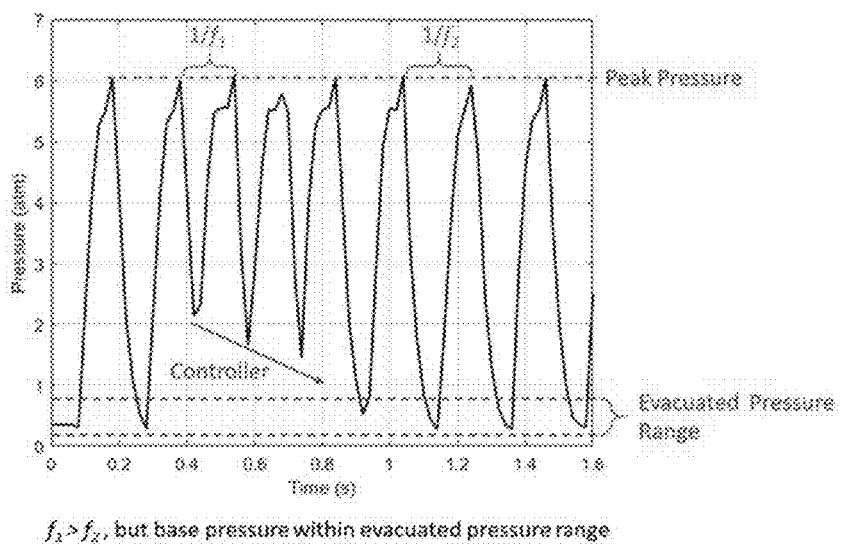

FIG. 21 is a graph illustrating that as frequency (or pressure difference) of the oscillations changes, a controller is used to ensure the balloon is evacuated to within a desired pressure range according to the principles of the present teachings.

Figure 22:
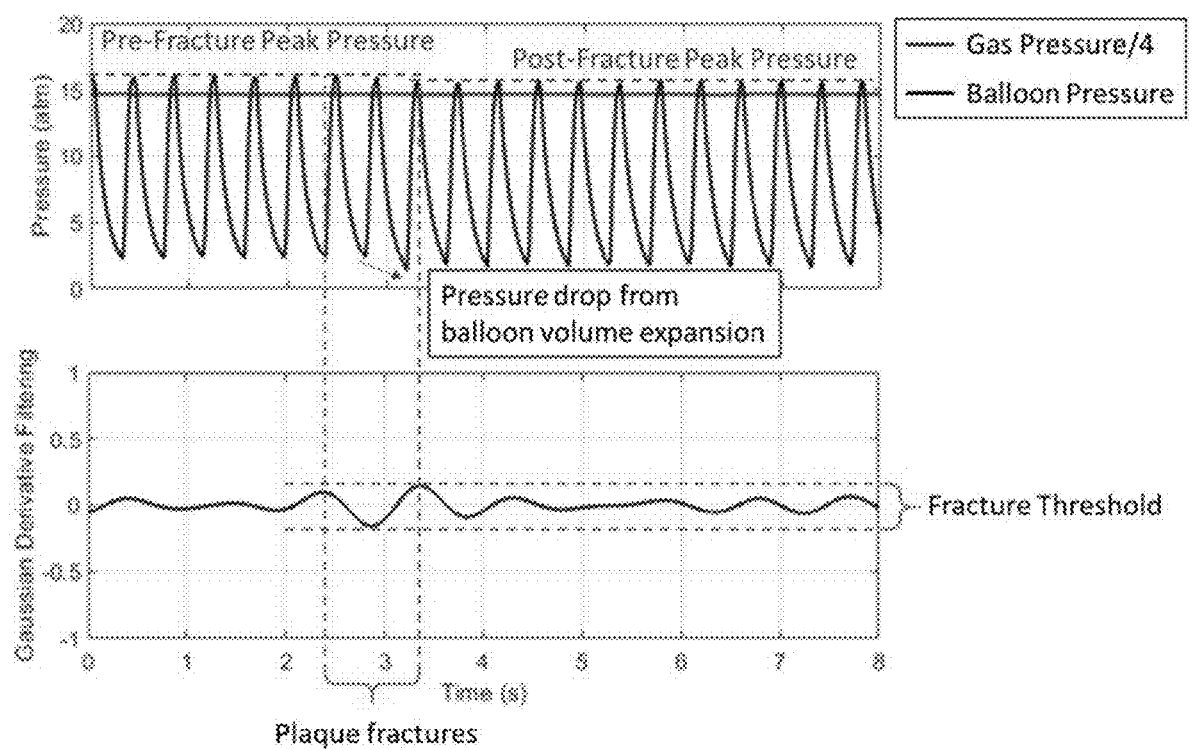

FIG. 22 is a graph illustrating a fracture of a material surrounding the balloon causes balloon volume expansion and a measurable diminution in pressure, which may be identified using data filtering techniques and compared to a fracture threshold. Subsequent to detecting fracture, the oscillatory system may be shut off or the pressure may be reduced depending on the desire of the physician.

Figure 23A:
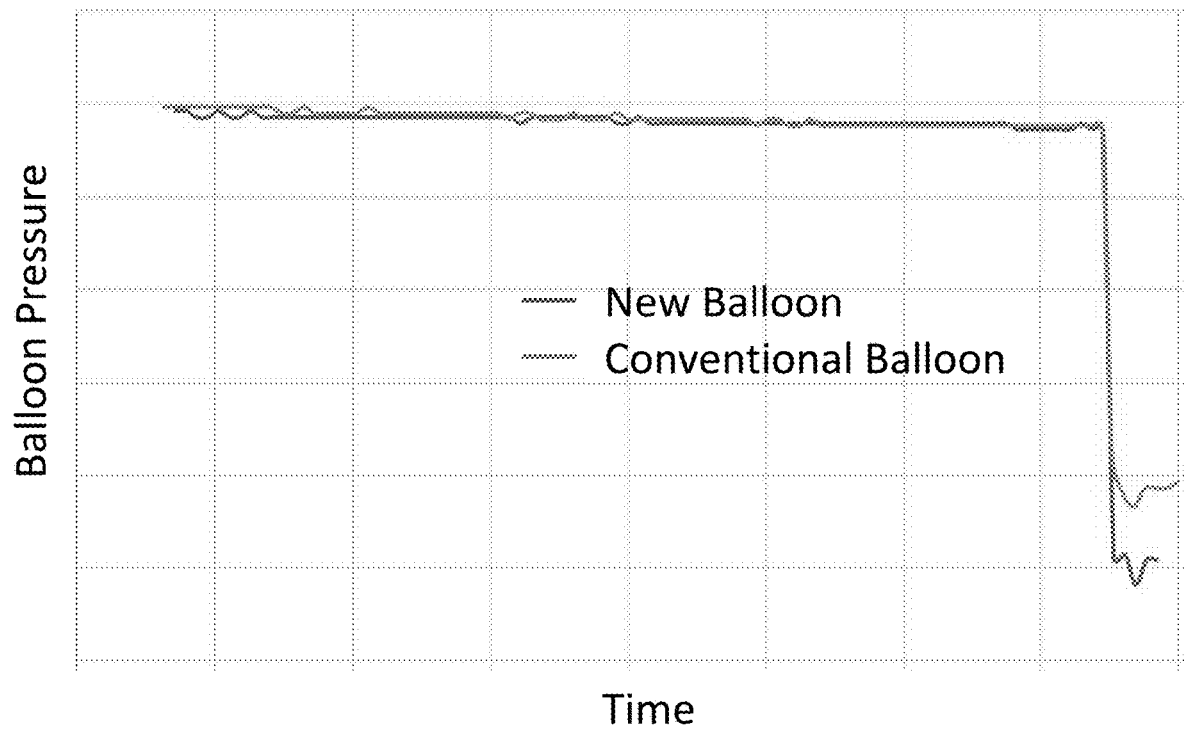

FIG. 23A is a plot of the pressure drop simulating calcified plaque fracture and indicating the improvement in back-sensing due to the exemplary angioplasty catheter with expanded flow lumen and braided shaft.

Figure 23B:
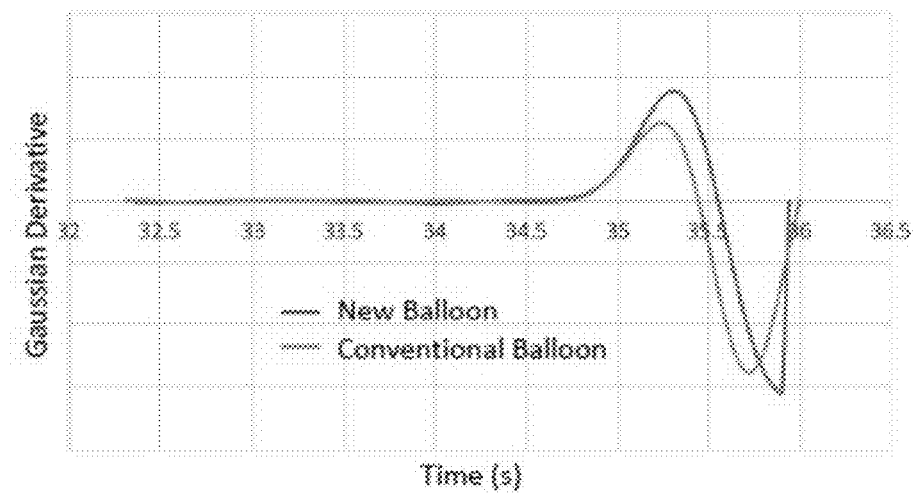

FIG. 23B is a plot of the Gaussian Derivative indicating an increase in magnitude of the derivative, which allows for improved sensing of balloon states such as expansion due to calcified plaque rupture.

Figure 24:
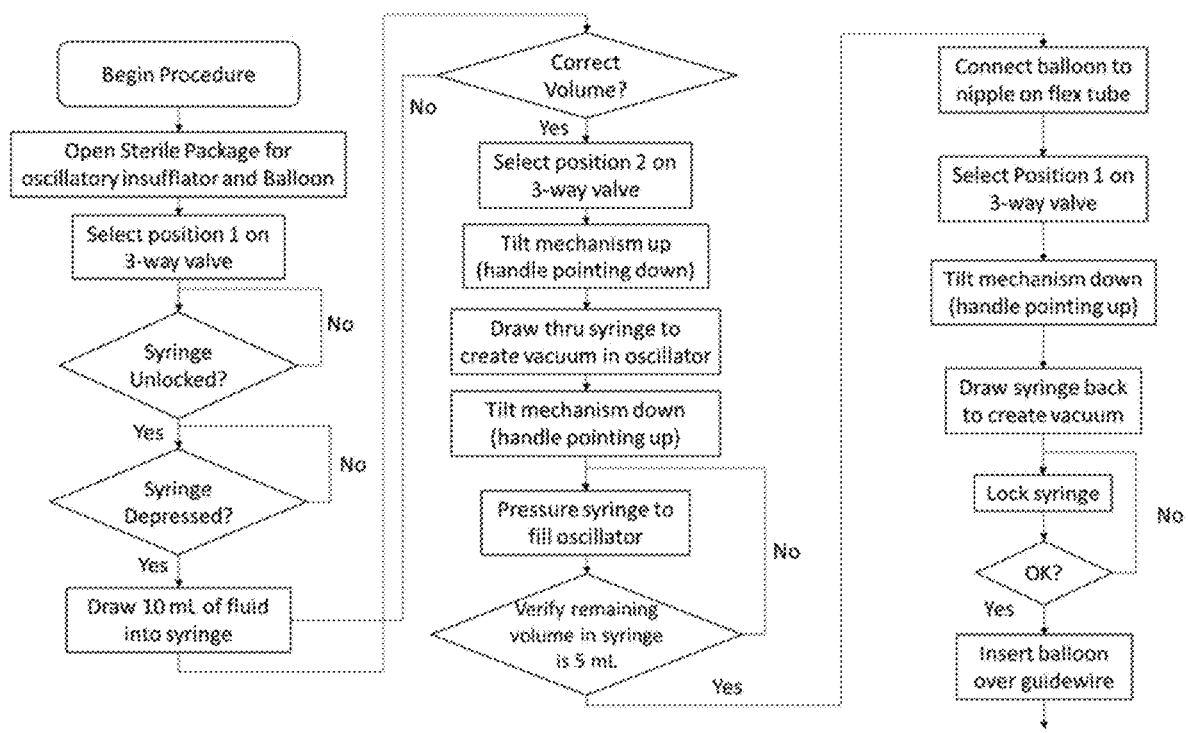

FIG. 24 is a process flow diagram according to the principles of the present teachings.

Figure 25:
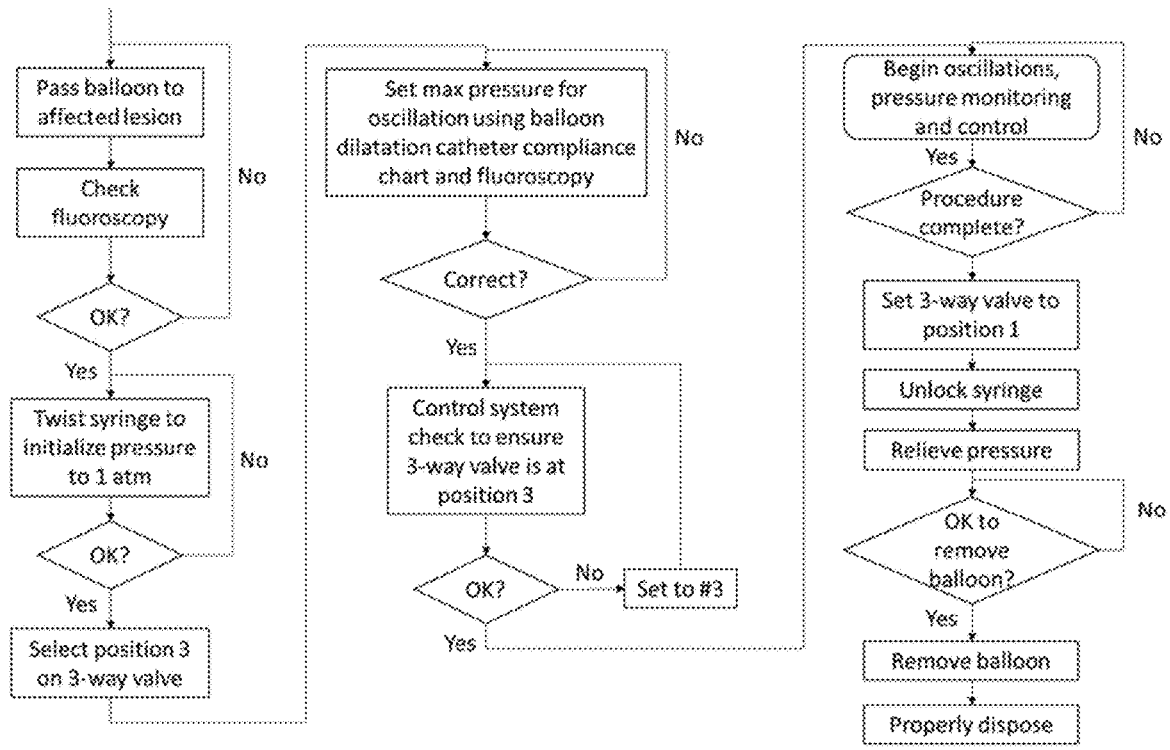

FIG. 25 is a process flow diagram according to the principles of the present teachings.

Figure 26:
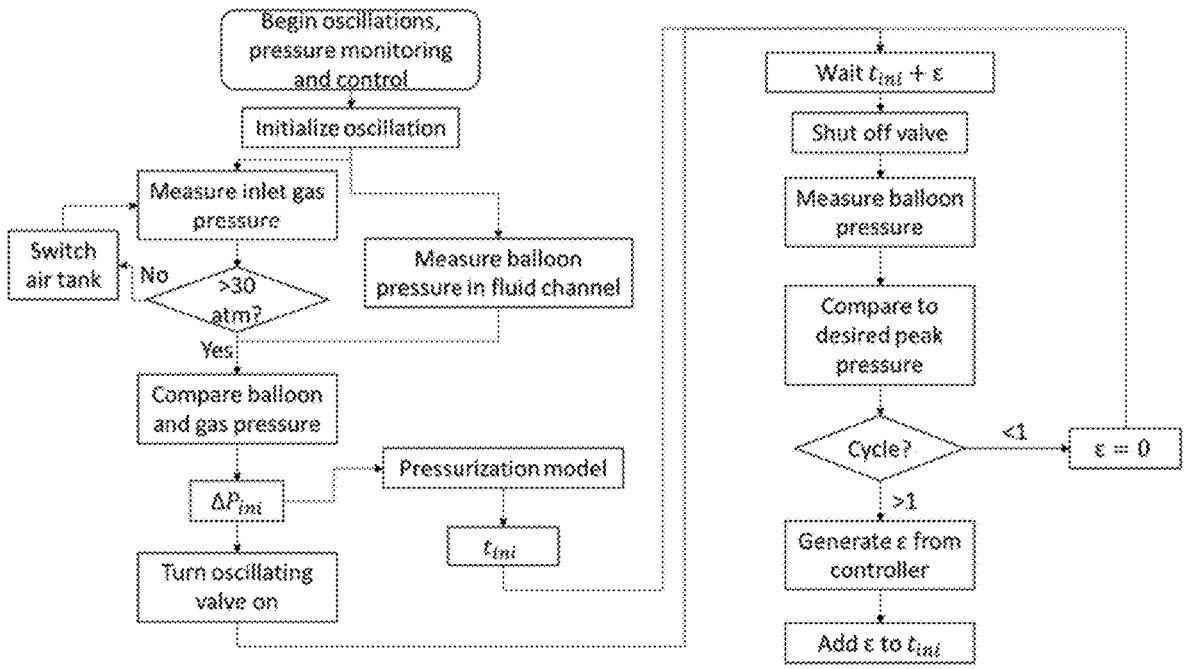

FIG. 26 is a process flow diagram according to the principles of the present teachings.

Figure 27:
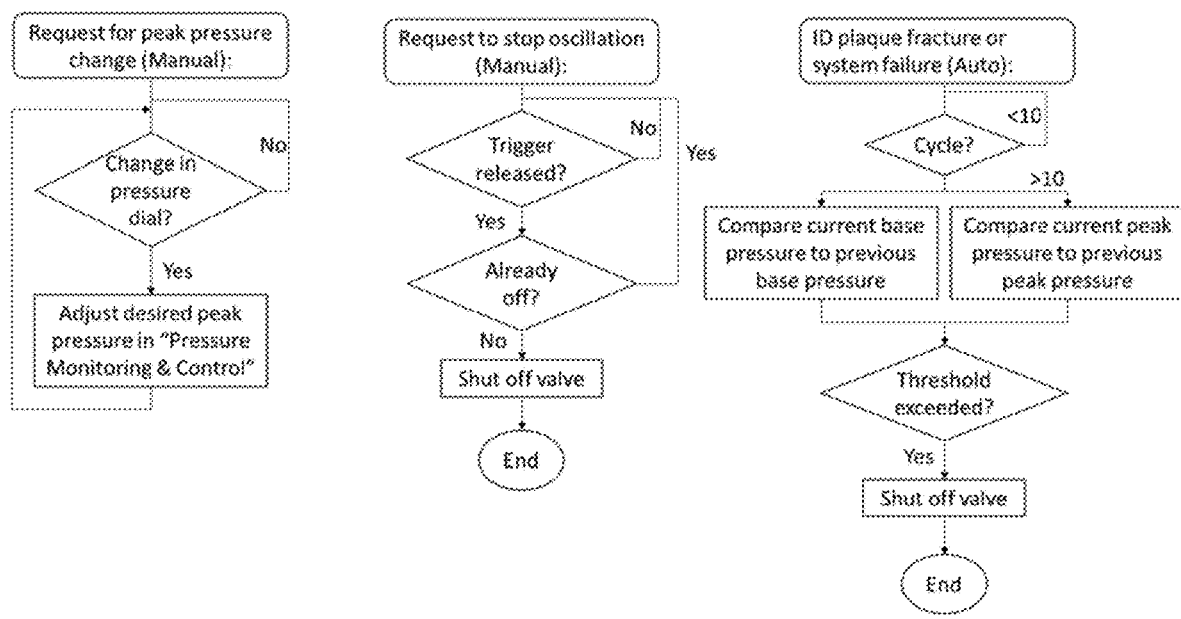

FIG. 27 is a process flow diagram according to the principles of the present teachings.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer, or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In accordance with the teachings of the present invention, a system embodiment for generating angioplasty balloon oscillations is provided. Generally, the system can comprise a high potential source such as a high voltage or pressure, a switching system for controlling high potential source, and a method for converting that potential into hydraulic oscillations of an angioplasty balloon. An embodiment of this system may be a disposable, oscillating balloon angioplasty pump 1 and a mounted, reusable unit 70.

As illustrated in FIGS. 4-8, in some embodiments, a dynamic balloon angioplasty pump system 1 (hereinafter "angioplasty unit 1") can comprise an angioplasty balloon inflation device 6, such as an angioplasty syringe (hereinafter generally "syringe"), an oscillating valve mechanism 14, a fluid communication path 35, a pneumatic communication path 36, and an electronic control unit 13.

In some embodiments, the syringe 6 can comprise a housing 12, plunger 33, screw-piston syringe handle 10, and screw-piston syringe latch 9. Translation of the syringe 6 induces a flow in the internal fluid and a subsequent increase in internal fluid pressure. The syringe 6 may operate in a locked or unlocked mode depending on the state of the screw-piston syringe latch 9. In the unlocked mode, the syringe handle 10 and plunger 33 are free to translate within the syringe housing 12. In the locked mode, the syringe handle 10 is locked such that the plunger 33 may only translate with the rotation of the syringe handle 10.

In some embodiments, the oscillating valve mechanism 14 can comprise a solenoid valve 4, pressure outlet port 8, pneumatic inlet port 50, and intensifier assembly 400. The intensifier assembly 400 is detachable from the solenoid valve 4. The intensifier assembly 400 can comprise a fluid chamber 51, pneumatic chamber 56, elastic diaphragm 30, and spring return 52. The pneumatic chamber 56 and fluid chamber 51 are separated by an elastic diaphragm 30. The spring return 52 acts to return the elastic diaphragm 30 to an initial state during pressurization and to prevent overstretching and rupture of the diaphragm 30. The intensifier assembly 400 may have different sizes and shapes to accommodate the fluid volume required for oscillating various sized balloons 2. For example, for peripheral or coronary balloons that contain smaller fluid volumes (i.e. 0.1-0.5 mL) compared to valvuloplasty balloons (i.e. 0.5-1.0 mL), the intensifier assembly 400 may comprise a fluid chamber 51 with a smaller volume, which would produce a smaller total volume change in the balloon 2.

Two fluid communications paths are defined within disposable, oscillating balloon angioplasty pump 1. The pneumatic chamber 56, the solenoid valve 4, gas inlet port 50, and exhaust port 8 are in pneumatic communication with each other via a pneumatic communication path 36. The gas in the pneumatic communication path 36 may be $CO_2$ or other high-pressure gas commonly used in catheterization labs. The angioplasty screw-piston syringe 6, fluid chamber 51, Luer Lock or other proprietary connector (hereinafter "balloon connector") 3, and a pressure transducer 31 are in fluid communication with each other via the fluid communication path 35. The fluid may be a contrast, saline, or other solution typically used in catheterization labs. Balloon connector 3 is connectable to an angioplasty balloon 2, which can be a customized or conventional angioplasty balloon.

In some embodiments, the oscillating valve mechanism 14 varies the pneumatic communication path and operates in two modes: ON and OFF mode. During the 'ON' mode, the gas inlet port 50 is connected to the pneumatic chamber 56. In this mode, the high inlet pressure at the gas inlet port 50 pressurizes the pneumatic chamber 56. The increase in pressure in the pneumatic chamber 56 deflects the elastic diaphragm 30 into the fluid chamber 51. Deflection of the elastic diaphragm into the fluid chamber 51 induces a flow and pressurization of the fluid pressure in the catheter 16 and balloon 2. During the 'OFF' mode, the pneumatic chamber 56 is connected to the exhaust port 8. In this mode, the high gas pressure in the pneumatic chamber 56 and the high fluid pressure in the catheter 16 and balloon 2 are exhausted. As the high gas pressure in the pneumatic chamber 56 exhausts through the pressure outlet port 8, the spring return 52 and high fluid pressure in the catheter 16 and balloon 2 deflect the elastic diaphragm 30 into the pneumatic chamber 56.

A fluid communication valve 34 may be a three-way valve that separates the syringe 6, fluid chamber 51, and catheter 16 and balloon 2 fluid communication pathway 35. The valve has three positions: "Position 1," "Position 2," and "Position 3." Position 1 connects syringe 6 to the catheter 16 and the balloon 2, Position 2 connects syringe 6 to the fluid chamber 51, and Position 3 connects the fluid chamber 51 to the catheter 16 and the balloon 2. The pressure transducer 31 is distal to the fluid communication valve 34 and is in fluid communication with the catheter 16 and balloon 2.

Figure 9:
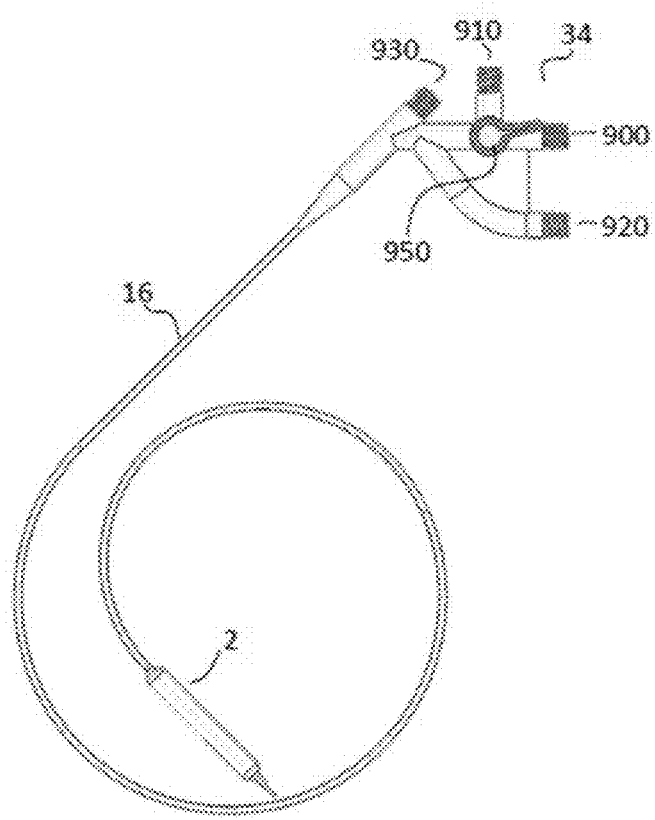
FIG. 9 is a front view of a four-port connector with an angioplasty balloon catheter.

In some embodiments, the fluid communication valve 34 may have four ports in a configuration to provide ease-of-use to the clinician, added safety to the procedure, and a quick-exchange between syringe-mode (Position 1) and oscillator-mode (Position 3) for fast balloon depressurization. FIG. 9 shows one arrangement of the fluid communication valve. In this arrangement, four ports are shown: (1) oscillatory-mode port 900, (2) syringe-mode port 910, (3) pressure sensor port 920, and (4) guidewire port 930. The ports may have a Luer Lock screw with male or female ends, snap connectors, or other connection type. In this arrangement, a three-way valve 950 connects the catheter 16, the syringe 6, and the oscillating mechanism 14. The three-way valve may be a spring-loaded return valve, a pressable button valve, one-way valve, electronic valve, or other valve configuration. In this arrangement, the valve 950 has three positions: "Position 1," "Position 2," and "Position 3." Position 1 connects syringe 6 to the catheter 16 and the balloon 2, Position 2 connects syringe 6 to the fluid chamber 51, and Position 3 connects the fluid chamber 51 to the catheter 16 and the balloon 2. In this arrangement, the pressure sensor port 920 is in constant fluid communication with the catheter 16 and balloon 2 regardless of the valve position. With the pressure sensor in this position, the electronic unit 13 may constantly monitor the balloon pressure during the procedure. Additionally, it can prevent damage to the internal elastic diaphragm 30, which may occur if oscillations are enabled when the valve is in Position 2. In this case, the pressure oscillations would be transmitted to the syringe 6, and the pressure transducer 31 would not detect these pressure oscillations or increases. When this occurs, the electronic unit 13 would detect the lack of pressure increase and the system would safely shut off and reduce pressure. In another case, after the oscillatory treatment, the clinician could forget to depressurize the balloon, which can only occur when the syringe is released, and Position 1 is set on the valve 950. When this occurs, the electronic unit 13 would detect the prolonged high pressure in the balloon and inform the clinician using a sound or light indicator to check the valve 950 to ensure the balloon was depressurized. Additionally, since the connector 34 may be directly attached to the catheter 16, it will restrict other non-compliant balloons from connecting into the oscillatory mechanism 16. With this restriction, the system will have an added safety benefit wherein other non-approved or off-label balloons may not be used with the system.

Figure 10:
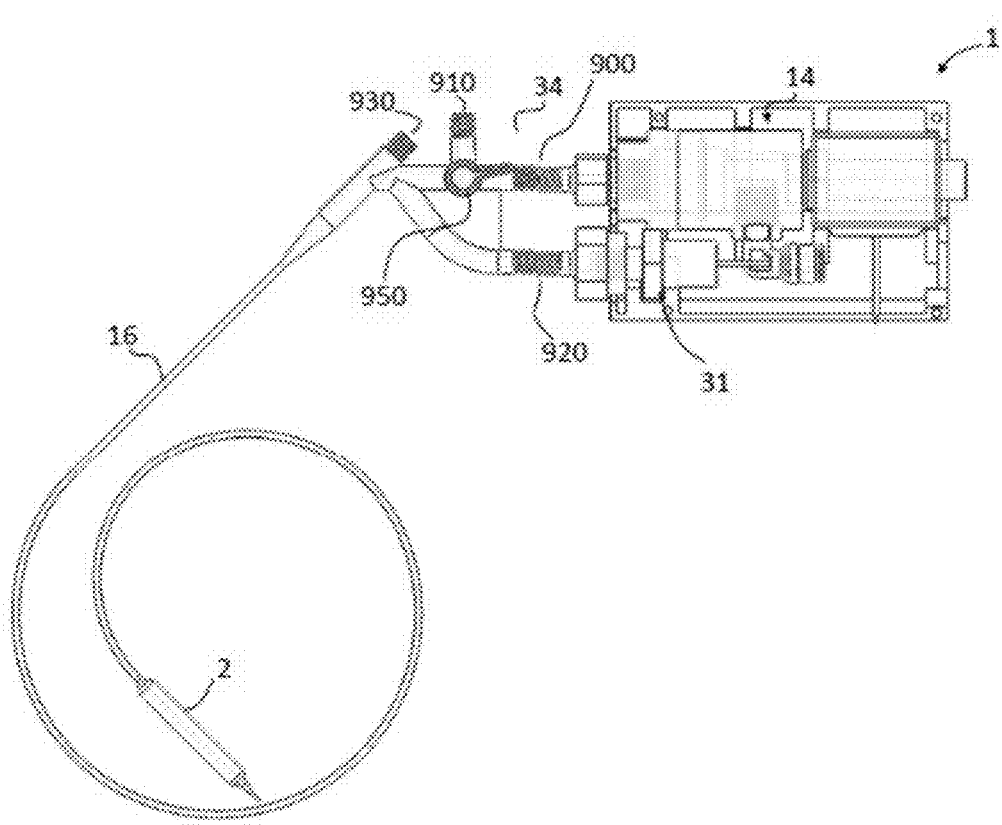
FIG. 10 is a broken-away front view of a disposable device that connects to the four-port connector of FIG. 9.

In some embodiments, the connector assembly 34 may be used with the disposable assembly 1 of FIG. 10 and a conventional off-the-shelf syringe 6. In this embodiment, the oscillator mechanism 14 and balloon pressure transducer 31 are configured into a stacked or side-by-side configuration to accept the connector assembly 34. In this case, the syringe 6 is not required to be integrated into the disposable oscillator but can be an off-the-shelf syringe 6 that is connected into the connector assembly 34. Using an off-the-shelf syringe 6 significantly reduces assembly, development, and regulatory costs and allows hospitals to keep some of their typical equipment.

In some embodiments, the electronic unit 13 manages the power, control, sensing, and communication requirements for the angioplasty unit 1. The electronic unit 13 may comprise a pressure transducer 31, an LCD screen 11, a power and communications connector 7, and an electronic control board 32. The power and communications connector 7 powers the electronic unit 13 and the solenoid valve 4 and manages incoming and outgoing signals to and from the angioplasty unit 1. The electronic control unit 32 can provide signal and power control to achieve the solenoid valve 4 modes described previously. A pressure transducer 31 measures the fluid pressure in the catheter 16 and balloon 2 and outputs a corresponding signal. The pressure measurement signal is transferred to the electronic control board 32. The electronic control board 32 may measure the state of the fluid communication valve 34 via a limit switch or potentiometer, for example. The electronic control board 32 can display measured information on the LCD screen 11 such as fluid pressure, measured gas pressure, procedure time via an on-board clock, oscillation number and frequency, peak pressure setting, connection status, and fluid communication valve 34 status. The electronic control board 32 may measure the signal output of a potentiometer or push button on the angioplasty unit 1 to set control parameters such as peak pressure or oscillation frequency.

Figure 11A:
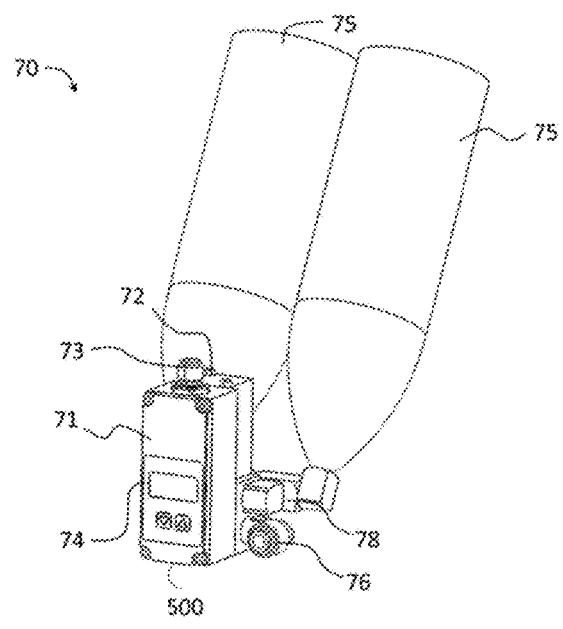
FIGS. 11A and 11B are isometric views of a two-part reusable device according to the principles of the present teachings.
Figure 11B:
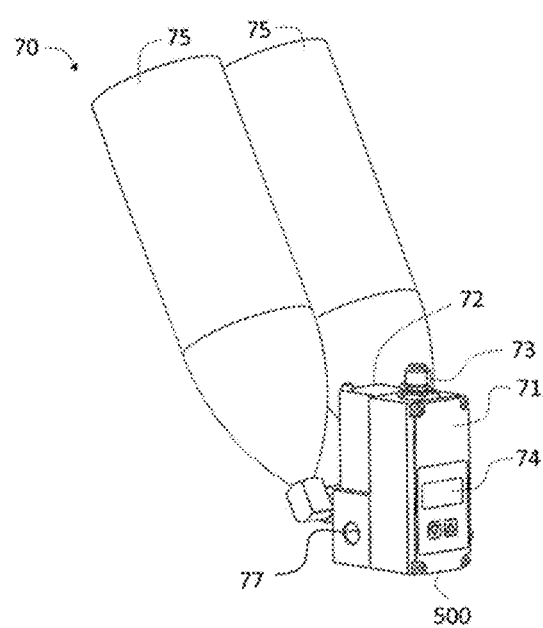

In accordance with the present teachings as illustrated in FIGS. 11A-11B, a mounted reusable unit (hereinafter "reusable unit") 70 may comprise a high-pressure gas pathway 78 and a control unit 72.

In some embodiments, a high-pressure gas pathway 78 of the mounted reusable unit 70 may comprise one or more pressure tanks 75, a regulator 71, high pressure (regulated or un-regulated) output 76 and exhaust port 77. The pressure tanks 75 supply high-pressure gas, such as $CO_2$, to the high-pressure gas pathway 78. From the high-pressure gas pathway 78, the high-pressure gas may be regulated to a desired pressure through regulator 71 with exhaust port 77. Regulated high-pressure gas or high-pressure gas directly from the pressure tanks 75 is ported through the high-pressure output port 76 and into the angioplasty unit 1 gas inlet port 50.

In some embodiments, a master control unit 72 of the mounted reusable unit 70 may comprise an LCD display screen 74, programmable logic controller (PLC) 500, and, communications and power output 73. The PLC 500 may serve as the master controller and communication hub for the reusable unit 70 and angioplasty unit 1. Functions of the programmable controller 500 may include controlling regulator output, controlling the solenoid modes, measuring gas pressure, comparing gas and fluid pressures, storing data, performing required checks, and outputting information to a larger display within the operating room. Other functions of the PLC 500 include ensuring safe operation such as verifying the state of the fluid communication valve 34 and monitoring the fluid pressure for indications of angioplasty unit 1 failure. Other functions of the PLC 500 include sensing fracture of the calcified plaque through a comparison of the fluid and gas pressures and a fracture threshold. The LCD display screen 74 may provide general information such as the state of the pressure tanks 75 or connectivity of the reusable unit 70 to the angioplasty unit 1. The communications and power output 73 may connect with the power and communications connector 7 on the angioplasty unit 1. Functions of the communications and power output 73 include sending and receiving communication signals from the angioplasty unit 1 such as solenoid mode, fluid pressure, and connectivity. Other functions of the communications and power output 73 include delivering the required power to the angioplasty unit 1.

Figure 12:
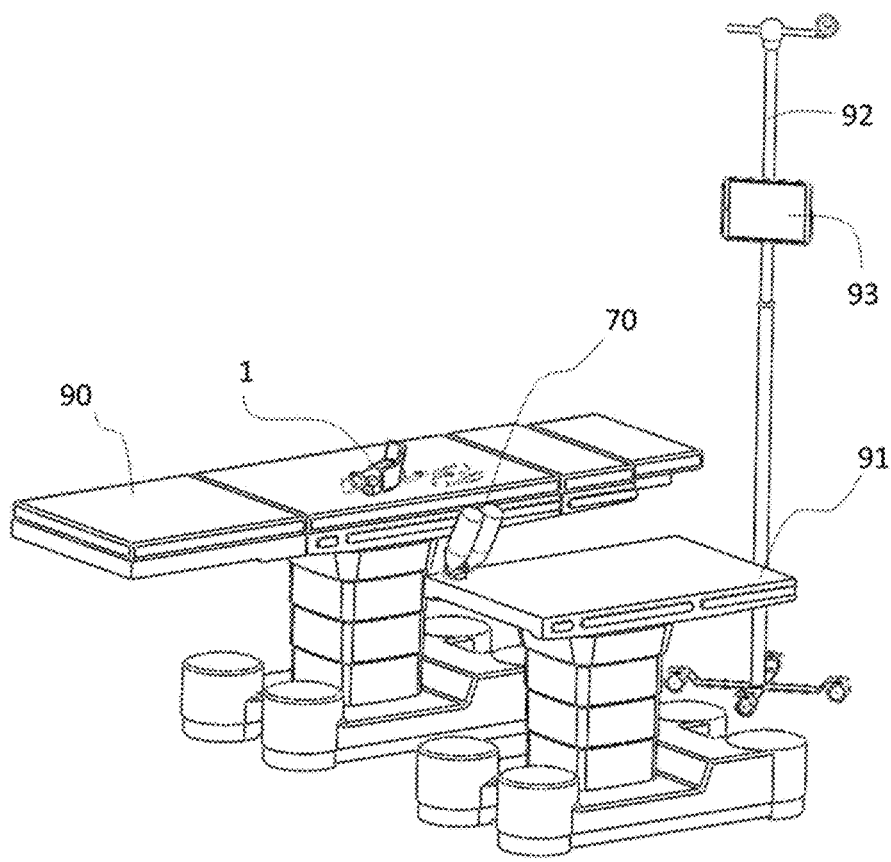
FIG. 12 is a perspective view of an operating room having the devices and/or mechanisms of the present teachings located therein.

FIG. 12 illustrates an ideal placement scenario within a catheterization lab according to some embodiments in which the reusable unit 70 is mounted on a surgical accessories cart 91. Other than pneumatic and electrical communication with the reusable unit 91, the reusable unit 70 is kept out of patient contact (i.e. separated from the operating table 90). The angioplasty unit 1 either is handled by the physician during the procedure or is placed on the table 90 during setup.

In some embodiments of the angioplasty unit 1, smaller high-pressure tanks 75 are integrated into a handheld disposable device 1. These tanks are filled to a high pressure and are communicated to the oscillating mechanism 14.

Figure 13A:
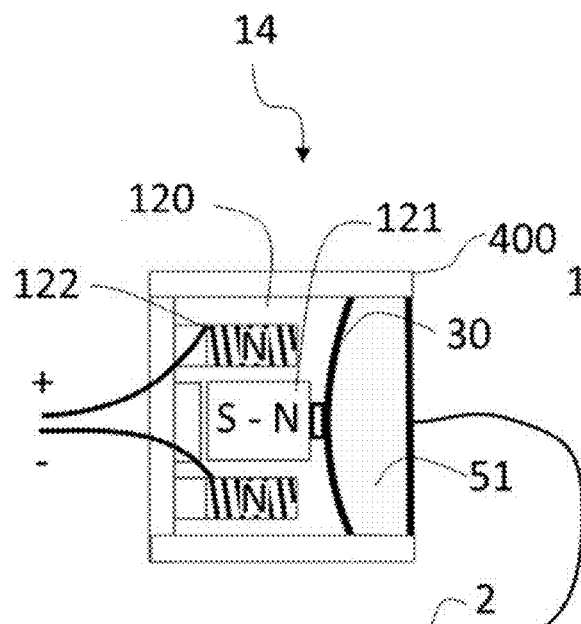
FIG. 13A is an exemplary arrangement of a second embodiment for generating oscillatory pressure (i.e. low pressure) in a balloon catheter according to the principles of the present teachings.
Figure 13B:
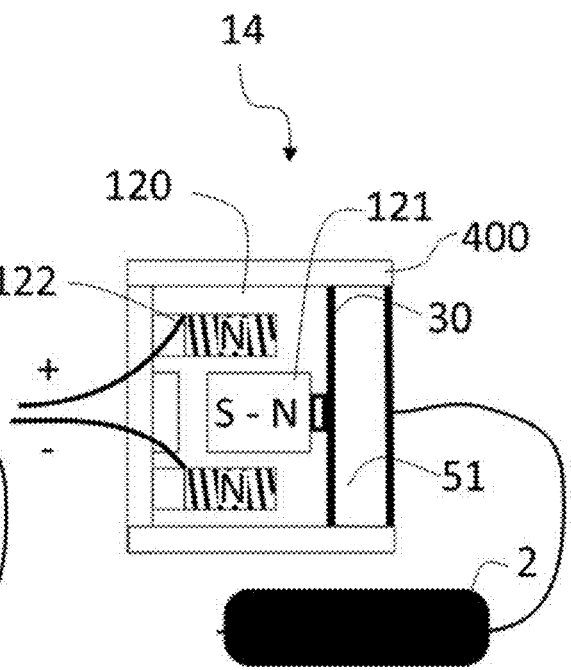
FIG. 13B is an exemplary arrangement of the second embodiment for generating oscillatory pressure (i.e. high pressure) in a balloon catheter according to the principles of the present teachings.

In some embodiments, as illustrated in FIGS. 13A-13B, the oscillating mechanism 14 may comprise a solenoid-driven actuator 120 that drives a pressure increase in the fluid chamber 51 and balloon 2 by the force generated in a magnetic or ferro-magnetic plunger 121 by an electromagnet 122. In this embodiment, an electromagnet 122 surrounds a magnetic or ferromagnetic plunger 121, which is fixed to the elastic diaphragm 30. When a current driven by a high voltage potential is provided to the electromagnet 122, the plunger 121 advances, deforms the diaphragm 30, and pressurizes the distal fluid chamber 51 and the angioplasty balloon 2. For a magnetic plunger, current in the electromagnet 122 can then be reversed to return the plunger 121 and depressurize the distal fluid chamber 51 and balloon pressure 2. For a ferromagnetic plunger, the plunger 121 and diaphragm 30 is returned to its initial position via a spring return. It should be understood that the present embodiment, along with additional embodiments disclosed herein, can serve as methods to generate hydraulic balloon pressure through a controlled release of high potential voltage, high pressure gas, and the like.

This embodiment, as opposed to the solenoid valve pneumatic-driven mechanism described above, does not require a high-pressure source, reduces noise from the high-pressure exhaust associated with the embodiment, controls the balloon inflation impulse time, and improves balloon deflation time.

To fracture calcified plaque, the pressure within the angioplasty balloon 2 should be oscillated at a high frequency. High frequency balloon oscillation improves the treatment of calcified plaque in two ways. Firstly, because the calcified material grows within healthy elastic tissue, the high frequency vibrations may grow microfractures in the calcified plaque, reduce its fracture strength, and reduce the energy (and damage) inputted into the surrounding healthy tissue. Secondly, since the overall time a vessel can be occluded is limited, a higher frequency of vibration leads to more energy being applied to the plaque in a shorter duration. Increasing the frequency in which the oscillations occur ensures that the plaque is subjected to more oscillations, thereby reducing its fracture pressure. As a rule of thumb, the time in which an angioplasty balloon can be inflated in a vessel is about 90 seconds in the peripheral arteries and 30 seconds in coronary arteries. From the present research, it has been found that the most calcified plaques generally require hundreds to thousands of oscillations of pressure cycles at frequencies between 2-40 Hz and maximum pressure oscillations between 0 and 20 atm.

With the pressure waveforms that are present in the prior art (FIG. 14A), the cycle times for a single pressure oscillation between 0 and 20 atm requires a minimum cycle time 142 of 10 seconds per oscillation. To achieve the thousands of cycles required to induce microfractures within calcified plaque 600 with the prior art, the procedure would require hours. Several reasons exist for the long cycle time of the prior art including a narrow and long flow channel in the catheter 16, the slow inflation and deflation times due to the conventional syringe 6, and the lack of control of the pressure cycle. In the prior art, the narrow and long flow channel in catheter 16 limits and attenuates the flow to the balloon 2. In the prior art, the syringe is hand-operated by a clinician, and therefore, the cycle times of pressure oscillations are limited by hand speed. The lack of control of the pressure cycle in the prior art does not allow the balloon 2 to rapidly achieve desired pressures in the cycle.

The increasing pressure portion of the waveform 140 follows a limited increase exponential function:

$$P_{balloon}(t) = (P_{high} - P_{balloon}(t))\left(1 - e^{-\frac{t}{\tau}}\right) \quad (1)$$

where $\tau$ is the balloon filling time constant dependent on the flow resistance of the flow channel in the balloon catheter and the balloon's pressure-volume relationship and t is the time from the start of the oscillation. The decreasing pressure portion of the waveform 141 follows a diminishing exponential function:

$$P_{balloon}(t) = (P_{balloon}(t_{fc}) - P_{vac})e^{-\frac{t-t_{fc}}{\tau}} \quad (2)$$

where $t_{fc}$ is the time at the start of deflation.

A more optimal pressure waveform, as generated by the described embodiments of the present teachings, is shown in FIG. 14B. To achieve this waveform, four modifications to the prior art were required: (1) high gas inlet pressure (on the order 20-300 atm), (2) spring loaded diaphragm, (3) flow area increase of the flow lumen in the catheter, and (4) control system for pressure cycling.

The first modification to achieve the more optimal waveform of FIG. 14B is to input a pressure with a magnitude on the order of 20-300 atm. This pressure is above the desired balloon peak pressure and is input into the inlet port 50 of the oscillator 4. Practically, the high-pressure gas can be regulated to this magnitude or can be ported directly from a central gas tank. According to Eq. (1), maintaining the gas pressure into the inlet port, $P_{high}$, at a higher pressure than the desired pressure, reduces the time to desired inflation by generating a near infinite slope 143 during the pressurization (FIG. 14B). The near-infinite slope generates a large pressure impulse in the balloon 2, which is apposed to the calcified plaque 600, causing the balloon 2 to inflate uniformly despite any calcified plaque obstruction. This uniform inflation distributes the stress applied by the balloon evenly to the surrounding plaque, as opposed to just the elastic tissue, ultimately inducing fatigue and microcrack growth in the plaque. Further, because the balloon 2 can inflate and distribute stress uniformly with this high impulse pressure, smaller balloon diameters may be used to reduce the elastic strain on the tissue.

Because the gas inlet pressure may be higher than the desired balloon pressure, the oscillation valve 14 is required to shut off as the balloon 2 reaches the desired inflation pressure. This shut-off time is controlled by the control mechanism, which is discussed in the next section, and may be located within the PLC 500 of the reusable unit 70 or the electronic control board 32 of the angioplasty unit 1. One benefit of using a control system to achieve the desired balloon pressure is to simplify the reusable unit 70 by removing the need for expensive pressure regulators that have limited pressure control ranges. However, not employing a pressure regulator leads to two issues: (1) a high inlet gas pressure and (2) a varying tank 75 pressure. High-pressure can cause damage to the oscillator 4 and other components. The issue may be solved by fabricating the oscillator 4 from high strength materials, such as stainless steels and composite-reinforced polymers. As gas is consumed and exhausted from the tank 75, the pressure in the tank decreases. Because the tank pressure may be used to pressurize the balloon, this varying pressure will affect the pressurization phase 143 of the cycle. The varying pressure from the tank issue is solved through control of the oscillator 4 mode. In the system, two pressure transducers are used to measure the inlet gas pressure and the balloon pressure. To control the balloon pressure with a varying input gas pressure, the gas pressure is measured continuously in the reusable unit 70 with a pressure transducer. The signal from the gas pressure transducer is measured by the PLC 500 and converted to gas pressure. The varying gas pressure and the peak balloon pressure are compared, and the time between oscillations is adjusted. For example, the time for a pressurization cycle 143 would be shorter for a higher tank pressure and longer for a lower tank pressure.

Another integral part to generating the waveform of FIG. 14B is the spring-loaded elastic diaphragm. For the decreasing portion 144 of the pressure curve, the gas and fluid pressure exhausts to atmosphere. During the de-pressurization, the pressure difference between the pressurized balloon 2 and the exhaust cannot be increased beyond the instantaneous balloon pressure, $P_{ball}$, minus the 1 atmosphere of vacuum, $P_{vac}$ (Eq. (2)). However, introducing a vacuum to the exhaust port increases the mechanism's complexity. Therefore, to improve balloon depressurization, a spring 52 is added in the fluid chamber 51 of the oscillator 14 to increase the back flow (i.e. to generate a vacuum). The spring stiffness and length can be adjusted to provide a balance between the increased resistance to the pressurization cycle and the generated vacuum during the inflation cycle. Further, the spring should be adjusted based on the size and shape of the intensifier assembly 400. For a peripheral or coronary balloon, the spring 52 may have a stiffness of 0.1-2 N/mm. The spring 52 may be stainless steel or other corrosion resistant metal.

Another integral part to generating the waveform of FIG. 14B is the increased flow channel size in the angioplasty catheter 16. An example cross-section of an angioplasty catheter is shown in FIG. 15. The catheter 16 may have a dual lumen construction with a guidewire lumen 700 and flow channel lumen 710. To reduce the entire cycle time 145, the hydraulic diameter of the angioplasty catheter 16 flow channel lumen 710 may be increased more than 20% compared to the conventional balloon catheter diameter. Increasing the effective area of the flow channel lumen 710 reduces the flow resistance by the fourth power. The area increase of the flow lumen 710, however, is constrained by a fixed outer diameter of the catheter 16 and the guidewire channel 700. For peripheral and coronary balloons, the outer diameter of the catheter 16 is 0.067". The guidewire channel 700 is suitable for passing a 0.034" guidewire. To increase the flow channel lumen 710, therefore, the guidewire lumen 700 may be reduced to accommodate a 0.014" guidewire.

FIG. 16 shows the force generated by a conventional angioplasty balloon with a narrow flow channel lumen being oscillated at 10 Hz with a peak pressure of 10 atm (6 mm diameter×60 mm length balloon dimensions and 75 cm shaft length). As shown, the waveform oscillates with a small amplitude because of the significant attenuation caused by the narrow flow channel and the relatively flexible shaft material. Also shown is that the peak pressure achieved by the conventional angioplasty balloon with a narrow flow channel is significantly lower than the force achieved during static pressurization of the balloon. The inability of the catheter to achieve the peak static force is due to the attenuation and fluid friction caused in the narrow flow channel of the conventional catheter.

Figure 1:
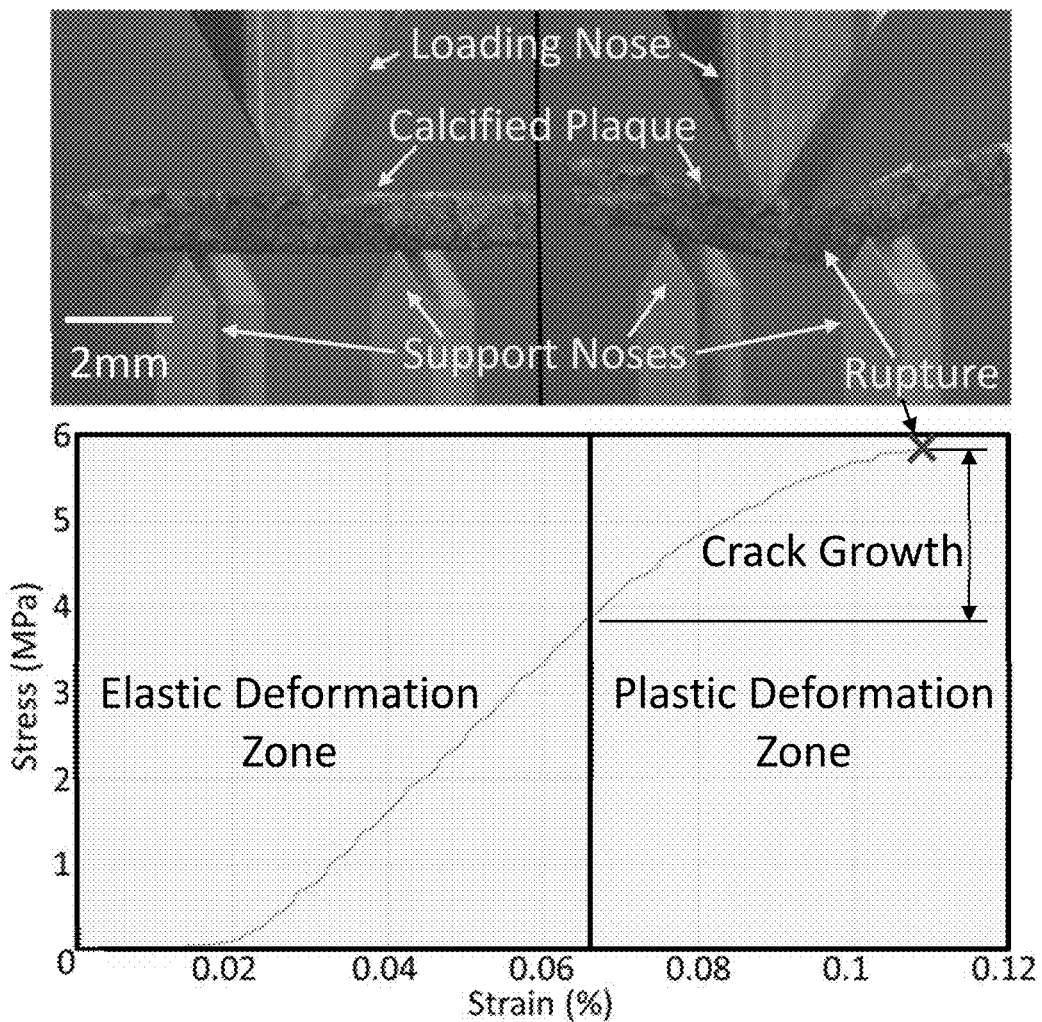
FIG. 1 shows a three-point bending test of calcified plaque before and after rupture and the corresponding stress-strain plot indicating the elastic and plastic deformation zone, the region of crack growth under the rupture stress, and the rupture stress.
Figures 2A, 2B, 2C, 2D, 2E:
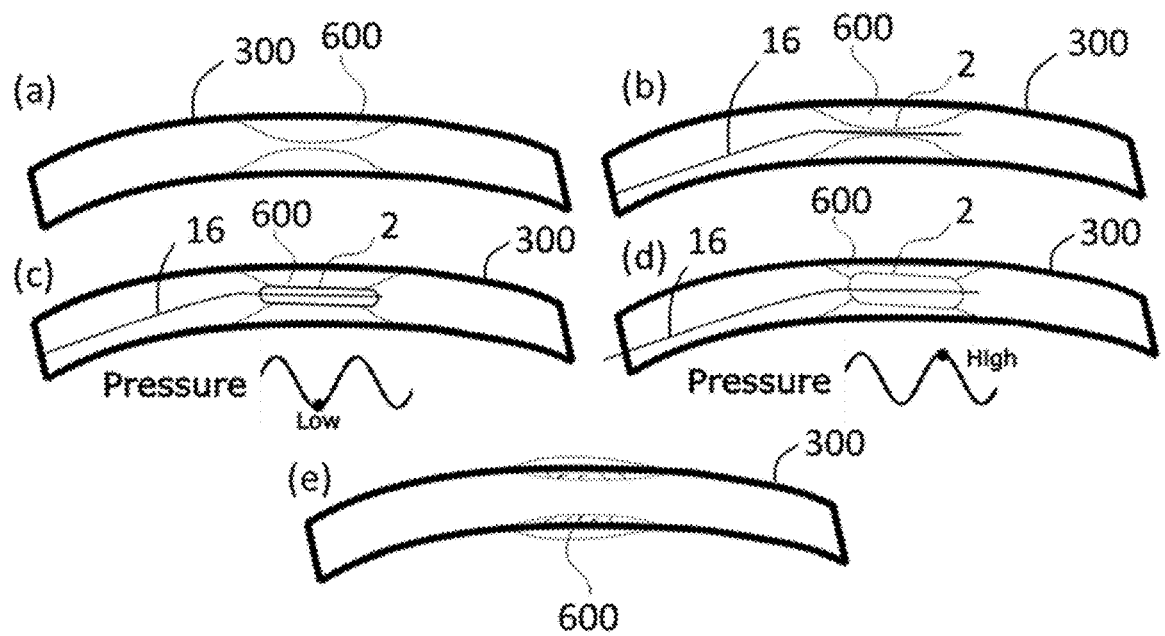
FIG. 2A is a schematic view of an elastic conduit (e.g. artery) having a hardened material (e.g. calcified plaque) embedded therein to be treated by the dynamic balloon angioplasty (DBA) techniques and devices according to some embodiments of the present teachings.
FIG. 2B is a schematic view of the elastic conduit of FIG. 2A having a DBA angioplasty balloon navigated to the affected region and pre-pressurized.
FIG. 2C is a schematic view of the elastic conduit of FIG. 2A having the DBA angioplasty balloon cycled to a low pressure.
FIG. 2D is a schematic view of the elastic conduit of FIG. 2A having the DBA angioplasty balloon cycled to a high pressure.
FIG. 2E is a schematic view of the elastic conduit of FIG. 2A having the hardened material fractured according to the principles of the present teachings.
Figures 3A, 3B:
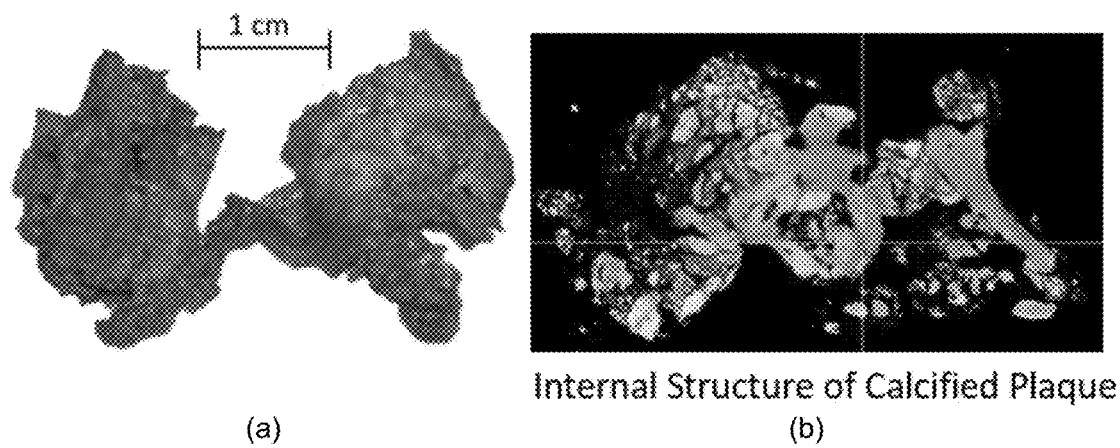
FIG. 3A is an image of a human femoral artery calcified plaque.
FIG. 3B is a high-resolution computed tomography (X-ray) internal cross-section demonstrating the microcracks and sharp corners in the internal structure of the human femoral artery calcified plaque.
Figure 4:
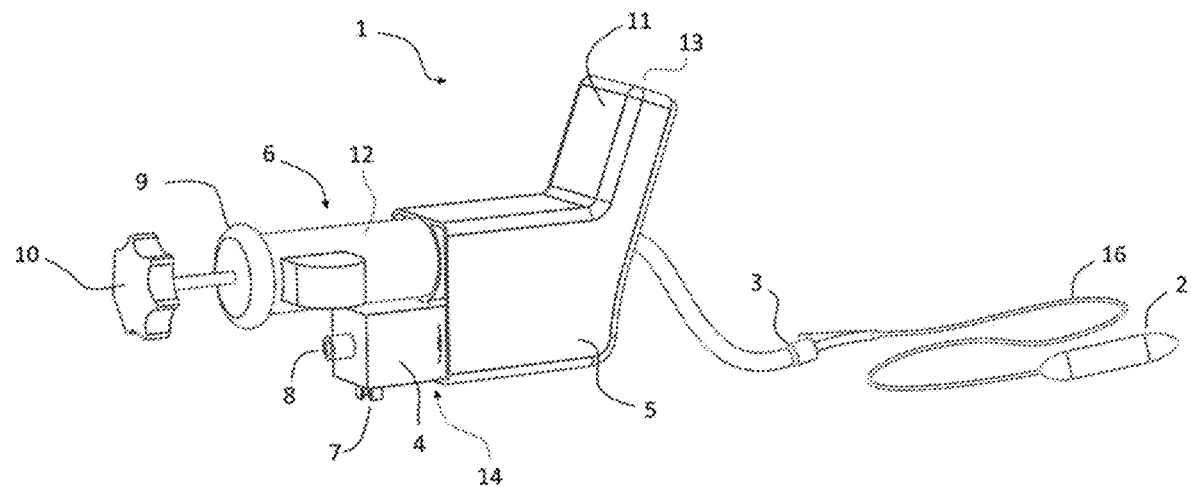
FIG. 4 is an isometric view of a handheld two-part disposable device according to the principles of the present teachings.
Figure 5:
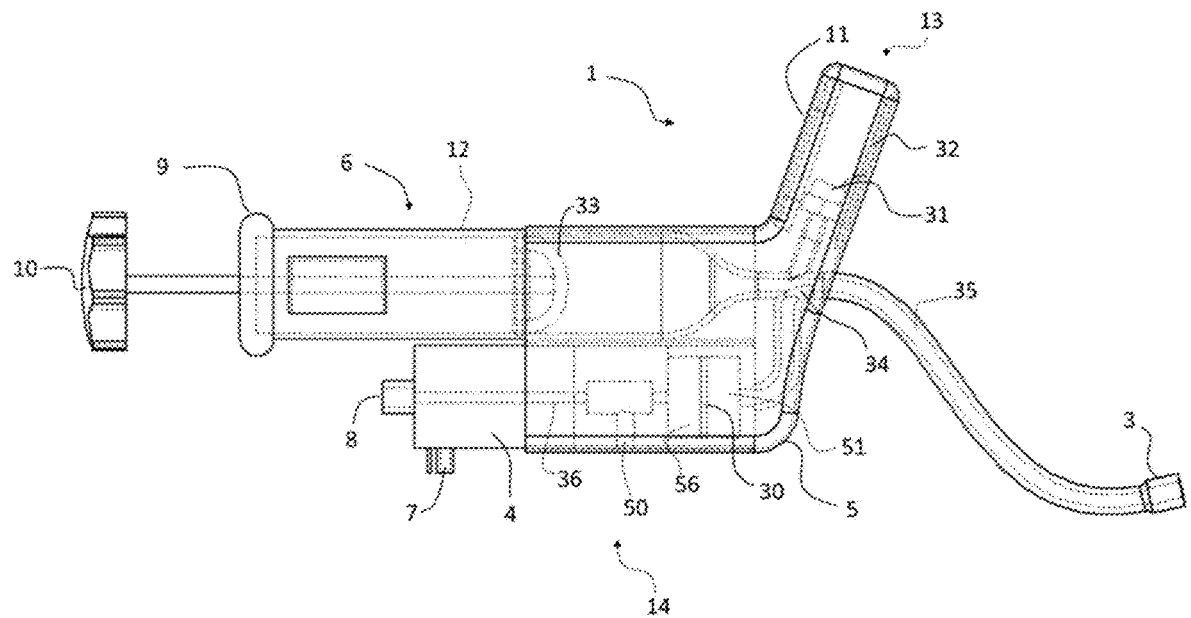
FIG. 5 is a side view of the handheld two-part disposable device according to the principles of the present teachings.
Figure 6:
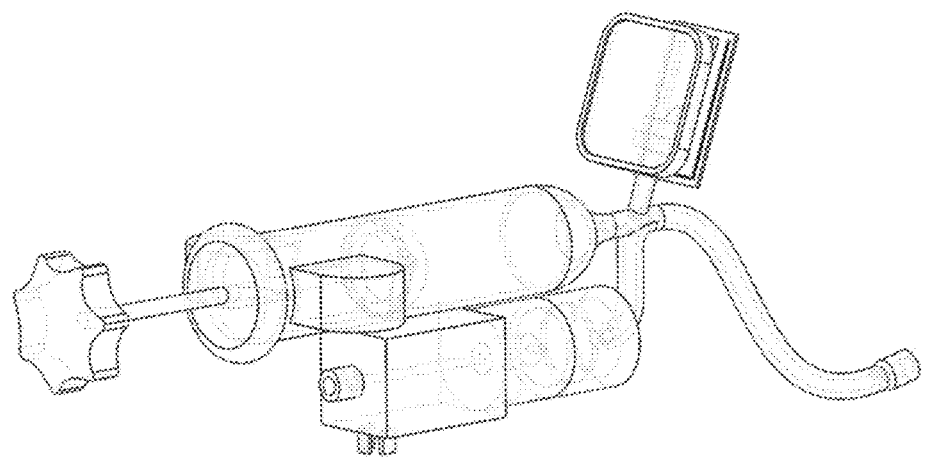
FIG. 6 is an isometric view of the handheld two-part disposable device without a cover according to the principles of the present teachings.
Figure 7:
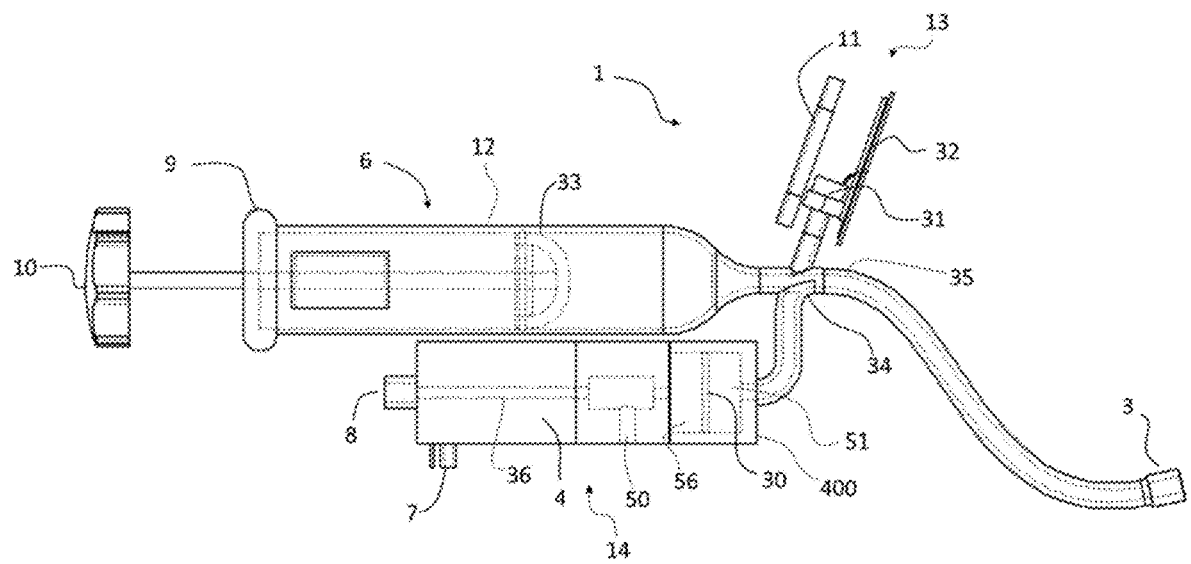
FIG. 7 is a side view of the handheld two-part disposable device without the cover according to the principles of the present teachings.
Figure 8:
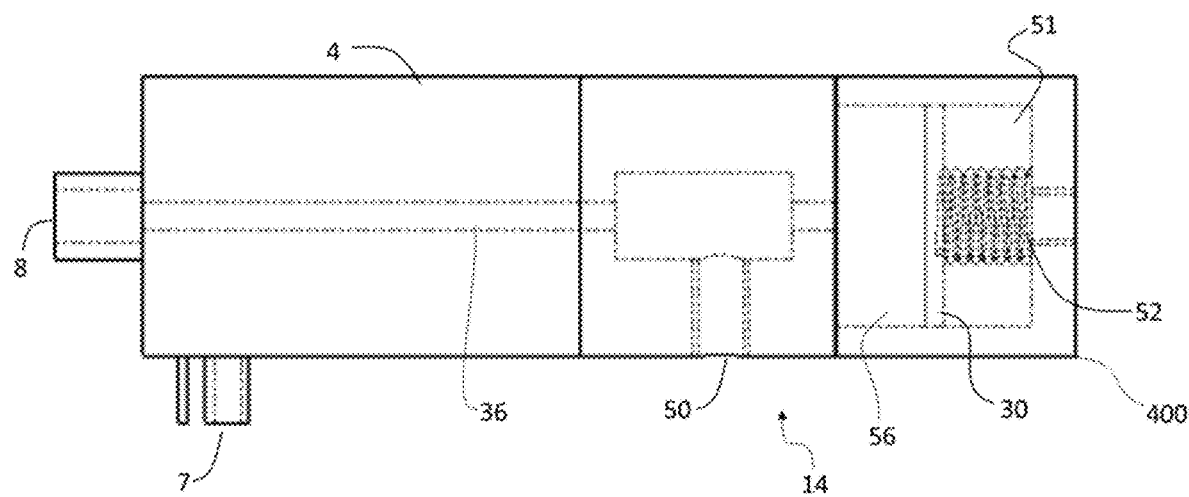
FIG. 8 is an enlarged side view of an oscillating valve mechanism according to the principles of the present teachings.

FIG. 17 shows the force generated by the exemplary angioplasty balloon with expanded flow channel and braided catheter shaft being oscillated at 10 Hz with a peak pressure of 10 atm (6 mm diameter×60 mm length balloon dimensions and 75 cm shaft length). As shown, the waveform oscillates with a large amplitude from a low force to the high peak force. This peak force matches the force generated from a static pressurization of the balloon, indicating that the full pressure waveform can be achieved at the 10 Hz oscillation frequency. Therefore, by expanding the flow channel lumen and stiffening the shaft with a braided exterior, the desired oscillations can be achieved. The flow channel lumen may be expanded in several ways including increasing the outer diameter of the shaft, reducing the diameter of the internal guidewire channel, using a monorail guidewire system, using a dual extrusion shaft, and stiffening the angioplasty shaft material while reducing the wall thicknesses. Stiffening of the angioplasty shaft can be achieved by applying an exterior braid of metal or other material conducive to braiding, using stiffer materials, or altering the geometry of the shaft extrusion. FIG. 18(A-B) shows the force generated by the exemplary angioplasty balloon with expanded flow channel and braided catheter shaft being oscillated at 15, and 20 Hz with a peak pressure of 20 atm (6 mm diameter×60 mm length balloon dimensions and 75 cm shaft length). In the 15 Hz case (FIG. 18A), the balloon generates an oscillatory force amplitude of up to 80% of the total peak static pressure force (with static pressure set at 10 atm). In the 20 Hz case (FIG. 18C), the balloon generates an oscillatory force amplitude of up to 60% of the total peak static pressure force (with static pressure set at 10 atm). At 20 Hz, nearly 2000 oscillatory cycles can be applied to the calcified plaque to generate stresses in the plastic deformation zone of FIG. 1 to grow cracks in the calcified plaque and reduce its overall strength.

In addition to improving the transmission of pressure oscillations, the exemplary flow channel lumen allows pressure to be measured accurately proximal to the angioplasty balloon and catheter. Because the flow is significantly attenuated by the small flow channel of the conventional angioplasty balloons, pressure cannot be sensed accurately. This limitation with conventional balloons reduces accuracy of the oscillatory treatment and would require complex electronics to ensure that the balloon reaches the desired pressure.

In many procedures, a larger guidewire (0.035") is used to ensure the guidewire can pass to the affected lesion and to maintain position for the angioplasty balloon and shaft. Because the guidewire diameter may be reduced in the exemplary embodiment, the stiffer external angioplasty shaft material also serves to improve placement and navigation of the balloon catheter to the desired destination even with the smaller guidewire. This balance allows the clinician to reach difficult to treat locations while also being able to deliver the oscillatory treatment.

A larger waveform segment of a full angioplasty procedure with an oscillatory frequency of f and two peak pressures (Peak Pressure I and Peak Pressure II) is shown in FIG. 19. During the pressurization cycle, the solenoid valve 14 is in the ON mode. During the ON cycle, the control system waits for the pressure to rise to the desired peak pressure (e.g. Peak Pressure I or Peak Pressure II) before switching the solenoid valve 14 mode to OFF. During the depressurization cycle, the control system waits for the pressure in the balloon 2 to achieve a certain pressure range (i.e. below the evacuated pressure line) before switching the solenoid valve 14 mode to ON. The control algorithm constantly adjusts the timing, f, of the ON-OFF cycle time of the solenoid valve 14 to ensure that the pressure in the balloon is achieving the pressure and frequency as determined by the user or the control system. The ON 143 and OFF 144 cycle time can be adjusted separately to affect the frequency of the pressure waveform as well as the amplitude of the pressure waveform. The amplitude of the waveform is not limited to 0 to 100% of the inlet gas pressure. By varying the pressurization 143 and de-pressurization 144 cycle time, it is possible to achieve pressure peaks of 25%-75%, 50%-100%, or 0%-50% of the input gas pressure.

Achieving these oscillatory peak pressure amplitudes in the balloon requires precise pressure control. To ensure this precise control, a feedback and feedforward control algorithm may be used, as shown in FIG. 20. Alternatively, other controls algorithms such as state space or non-linear controls may be used. In the feedback and feedforward control algorithm shown in FIG. 20, a desired peak balloon pressure is determined by the clinician or derived based on imaging or prior data, which will herein be referred to as the "desired pressure". Also, a range for the deflation pressure is also known. During pressure cycling, pressure transducer 31 is used to measure fluid pressure in the balloon and a pressure transducer in the reusable unit 70 is used to measure the gas pressure. Using a balloon pressurization and de-pressurization model, such as those provided in Eq. (1) and Eq. (2) for a catheter 16 and the incoming gas pressure, a feedforward 'ON' mode time for the solenoid valve 14 is set. This feedforward setup reduces the load on the controller to set cycle times for achieving desired pressures, thereby increasing controller stability. During the oscillation, the balloon pressure is read and recorded at the time the oscillator switches OFF. This measurement is read and is compared with the desired balloon peak pressure to generate an error for feedback control. This error is then passed through a linear or non-linear controller to generate an error time $t_A$ for the oscillator. This delta ON-time, $t\Delta$, is added with the feedforward controller to generate the total on-time for the upcoming ON cycle.

For the OFF cycle, a similar method is used. However, the peak balloon pressure is used to determine OFF time in the feedforward system. The feedforward controller estimates the total OFF cycle time using a predefined model, such as those provided in Eq. (1) and Eq. (2). Once the solenoid valve 14 is switched to OFF, the pressure is recorded and compared with the pressure range. The error is then used to update the OFF cycle time duration, $t_A$, for the next OFF cycle.

An example use of the control algorithm is shown in FIG. 21. During the procedure, the balloon depressurization pressure falls out of the desired range. When this occurs, the controller works to reduce the frequency of oscillation such that the balloon has enough time to depressurize and reach the appropriate pressure range.

While tracking the balloon and gas pressure during the procedure, the control system also tracks the measurements for anomalies that would indicate calcified plaque fracture or system failure or leakage. As the angioplasty balloon 2 expands inside a calcified plaque lesion 600, it remains obstructed by the denser and stronger calcified plaque, which limits the expansion of the balloon 2 and reduces its overall volume. As the calcified plaque 600 is fractured and pushed into the artery wall 300, the balloon 2 can fully expand. This full expansion increases the total system volume reducing the overall system pressure. While the solenoid valve 14 is generating oscillations in the balloon 2, a sensing and filtering algorithm such as Gaussian Derivative Filtering or a Kernel function may be used to sense this decline in pressure, as shown in FIG. 22. In FIG. 22, the pressure in the balloon 2 achieves the desired peak pressure and depressurization range, but when fracture occurs, the waveforms shift down indicating a reduction in pressure due to an increase in system volume. This pressure drop can be sensed, compared to a fracture threshold, and used to shut off solenoid valve oscillation 14 of the angioplasty unit 1.

To improve the sensitivity of back-sensing of calcified plaque fracture, the exemplary angioplasty catheter described herein can be used. To demonstrate the effect of this catheter, a simulation of the improved back-sensing due to the increased flow channel lumen is shown in FIGS. 23A and 23B. A conventional angioplasty balloon and a balloon with an exemplary angioplasty catheter are pressurized to the same pressure and fracture (rapid balloon expansion) is simulated. Under similar conditions, there is an increased sensation from the pressure transducer of the pressure drop from the balloon with an exemplary angioplasty catheter (FIG. 23A). The corresponding Gaussian Derivative indicates a sharper and higher magnitude in the exemplary angioplasty balloon and catheter (FIG. 23B). Therefore, to improve back-sensing capabilities for sensing calcified plaque fracture, the exemplary angioplasty catheter can be used.

Procedural flow is shown in FIGS. 24-27. At the beginning of the procedure, sterile packages containing the angioplasty unit 1 and catheter 16 balloon 2 are removed from their package. The user connects the gas outlet port 76 and the communications and power port 73 on the reusable unit 70 to the gas inlet port 50 and the communications and power port 7 on the angioplasty unit 1. The user selects Position 1 on the 3-way valve 34, which connects the angioplasty insufflator syringe 6 to the distal flexible tube 3. The user checks if the syringe latch 9 is unlocked and unlocks the syringe 6 if locked. The user checks if the syringe plunger 33 is completely depressed and depresses the syringe handle 10 if not depressed. The user then inserts the flexible tube 3 into a fluid bath (e.g. saline or contrast) and draws 10 mL of fluid into the syringe 6. Upon verifying the correct volume in the syringe 6, Position 2 on the 3-way valve 34 is selected, connecting the syringe 6 to the oscillator 14. The angioplasty unit 1 is tilted up with the handle pointing down, and the syringe handle 10 is drawn to generate a vacuum and bleed air from the fluid chamber 51 of the oscillating valve mechanism 14. Before releasing the vacuum, the angioplasty unit 1 is tilted down with the syringe handle 10 pointing up to trap any air in the syringe 6. The syringe 6 is then pressurized to fill the oscillator until remaining volume in the syringe is 5 mL. The angioplasty catheter 16 and balloon 2 is then connected to the nipple on the flex tube 3. Position 1 of the 3-way valve 34 is selected to connect the balloon 2 to the syringe 6. The angioplasty unit 1 is tilted down with the syringe handle 10 pointing up and the syringe handle 10 is drawn to create a vacuum and to bleed the balloon 2. The syringe latch 9 is then locked to maintain vacuum in the balloon 2. The balloon 2 is inserted over a guidewire and is passed to the affected lesion 600 using fluoroscopy. Once at the balloon 2 is at the appropriate location, the balloon 2 is inflated to an initialization pressure of about 1 atm. Position 3 is set on the 3-way valve 34 to connect the oscillator valve mechanism 14 to the balloon 2. The desired peak oscillatory pressure is set by the clinician. The clinician should consult the balloon compliance chart and the fluoroscopy image prior to deciding the peak pressure. To ensure that the correct 3-way valve position 34 is selected, the electronic control board 32 may check to ensure that Position 3 is selected on the 3-way valve. This check may occur via a limit switch or a potentiometer attached to the 3-way valve 34. When ready, the physician requests oscillations to begin. During oscillations, gas inlet pressure is measured to ensure that the gas pressure of the tanks 75 is high enough for the procedure. If it is too low, the gas tanks 75 need to be refilled. In parallel, balloon pressure is measured using pressure transducer 31. The balloon and gas pressures are compared to generate an initialization pressure value, $P_{ini}$. $P_{ini}$ is used in a feed-forward pressurization model (i.e. Eq (1)) to determine the time until the balloon 2 is fully inflated. The solenoid valve 4 is turned on, and the system waits $t_{ini}$-$t_\Delta$ before shutting off. For the first cycle, $t_\Delta=0$. The valve is shut off, and simultaneously, the balloon pressure is measured to determine measured peak pressure. The measured peak pressure is compared to desired peak pressure, and the difference between the two values is recorded. This difference is fed into a controller, such as in FIG. 20, to estimate a time error, $t_\Delta$, that will reduce the difference between measured peak pressure and desired peak pressure. This process cycles until the procedure is complete. During the procedure, the physician can adjust the desired peak pressure to be higher or lower or request for the procedure to be completed. Other methods in which the procedure may be concluded include identification of plaque fracture or system failure, as described above. Once the procedure is complete, Position 1 on 3-way valve 34 is selected, the syringe latch 9 is unlocked, and the pressure is relieved. Once the balloon 2 de-pressurized, the clinician can remove the balloon 2 and catheter 16. The angioplasty unit 1 may be used again on the same patient during the same procedure by following the same procedural steps. Alternatively, similar procedural steps may be used if a different balloon is required. Upon completion of the entire procedure, the angioplasty unit 1 is discarded. Steps in this procedural flow may be varied in whole or in part depending on the preference of the user.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A dynamic balloon angioplasty system for applying a dynamic pressure to fracture or modify hardened materials embedded within an elastic conduit, the dynamic balloon angioplasty system comprising:
    a pressure source system configured to output at least a first predetermined pressure from a pressure source outlet;
    an angioplasty unit being fluidly coupled to the pressure source outlet to receive at least the first predetermined pressure, the angioplasty unit having an angioplasty inflation device and a balloon connector operably coupled to and extending from the angioplasty inflation device, the balloon connector being configured to be connectable to an angioplasty balloon for delivering a plurality of pressure pulses to the angioplasty balloon;
    an oscillating mechanism fluidly coupled to the pressure source outlet and the angioplasty balloon via a fluid communication path and being selectively actuated to receive pressure from the pressure source outlet and output the plurality of pressure pulses to the angioplasty balloon via the fluid communication path;
    a pressure transducer operably coupled to the fluid communication path, the pressure transducer measuring a fluid pressure within the fluid communication path and outputting a pressure signal; and
    a control system operably coupled to at least one of the pressure source system and the oscillating mechanism, the control system configured to determine an optimal hydraulic pressure oscillation frequency and amplitude for a given procedure and output a control signal to the oscillating mechanism, the control system further configured to accept a user-defined peak pressure value to limit a peak pressure within the angioplasty balloon, the control system further configured to monitor the pressure signal to detect fracture of the hardened material within the elastic conduit or system failure or leakage.

2. The dynamic balloon angioplasty system according to claim 1, wherein the pressure source system comprises:
    at least one pressure tank having a pressurized fluid at a pressure higher than a peak balloon pressure; and
    a pressure outlet system operably coupled between the at least one pressure tank and the oscillating mechanism.

3. The dynamic balloon angioplasty system according to claim 2, wherein the pressure source system is configured to output pressure between 0 to 300 atm.

4. The dynamic balloon angioplasty system according to claim 1 wherein the angioplasty unit, the pressure transducer, and a display device are operably coupled in a unitary assembly, the unitary assembly being releasably connectable to the pressure source system.

5. The dynamic balloon angioplasty system according to claim 1 wherein the angioplasty unit, the pressure transducer, and the control system are operably coupled in a unitary assembly.

6. The dynamic balloon angioplasty system according to claim 1 wherein the angioplasty unit, the pressure transducer, and a display device are operably coupled in a unitary assembly, the unitary assembly being releasably connectable to the pressure source system.

7. The dynamic balloon angioplasty system according to claim 1 further comprising a display device operably coupled to at least one of the pressure source system and the angioplasty unit.

8. The dynamic balloon angioplasty system according to claim 7 wherein the display device is wirelessly coupled to at least one of the pressure source system and the angioplasty unit.

9. The dynamic balloon angioplasty system according to claim 1 wherein the angioplasty unit further comprises an ejectable and exchangeable power supply.

10. The dynamic balloon angioplasty system according to claim 1 wherein the pressure source system comprises a pressure-regulated high-pressure gas source.

11. The dynamic balloon angioplasty system according to claim 1 wherein the control system is configured to monitor the pressure signal to detect fracture or modification of the hardened material within the elastic conduit by determining an overall diminution of pressure due to an increase in volume of the balloon.

12. The dynamic balloon angioplasty system according to claim 1 wherein the control system is configured to monitor the pressure signal to detect fracture of the hardened material within the elastic conduit by comparing pressure oscillations before and after the fracture, the pressure oscillations being at a lower average pressure than before the fracture.

13. The dynamic balloon angioplasty system according to claim 1 wherein the control system is configured to determine an optimal hydraulic pressure oscillation frequency and optimal hydraulic pressure magnitude for a given procedure and output a control signal to the oscillating mechanism.

14. The dynamic balloon angioplasty system according to claim 1 wherein the angioplasty inflation device is a lockable screw-piston-type syringe.

15. The dynamic balloon angioplasty system according to claim 1, wherein the first predetermined pressure comprises a pressure between 2 to 300 atm.

16. The dynamic balloon angioplasty system according to claim 1, wherein the system is configured so the angioplasty balloon is inflated at a frequency of between 2 to 40 Hz.

17. The dynamic balloon angioplasty system according to claim 1, wherein the system is configured so a peak pressure in the angioplasty balloon is substantially the same as the fluid pressure within the fluid communication path.

18. The dynamic balloon angioplasty system according to claim 1, wherein the balloon connector is configured to reduce flow resistance of delivering the plurality of pressure pulses to the angioplasty balloon.

19. The dynamic balloon angioplasty system according to claim 18, wherein the balloon connector comprises an expanded flow channel or a stiffened catheter shaft or a braided catheter shaft.

20. The dynamic balloon angioplasty system according to claim 1, wherein the oscillating mechanism comprises a solenoid valve and deformable diaphragm system fluidly coupled to the pressure source outlet, the solenoid valve being configured to switch from a high-state to a low-state, in the high-state, a high-pressure from the pressure source outlet is connected to the deformable diaphragm that separates a pressure source side and a hydraulic side, in the low-state, the pressure source side is exhausted to atmospheric pressure, the solenoid valve selectively outputting the first predetermined pressure and a second predetermined pressure from the pressure source outlet.

21. The dynamic balloon angioplasty system according to claim 20, wherein the deformable diaphragm is a spring-loaded elastic diaphragm configured to accelerate depressurization of the angioplasty balloon.

22. A dynamic balloon angioplasty system for applying a dynamic pressure to fracture hardened materials embedded within an elastic conduit, the dynamic balloon angioplasty system comprising:
  a pressure source system configured to output at least a first predetermined pressure from a pressure source outlet, the pressure source system being selectively actuated to output a plurality of pressure pulses;
  an angioplasty unit being fluidly coupled to the pressure source outlet to receive the plurality of pressure pulses, the angioplasty unit having an angioplasty inflation device and a balloon connector operably coupled to and extending from the angioplasty inflation device, the balloon connector being configured to be connectable to an angioplasty balloon for delivering the plurality of pressure pulses to the angioplasty balloon via a fluid communication path;
  a pressure transducer operably coupled to the fluid communication path, the pressure transducer measuring a fluid pressure within the fluid communication path and outputting a pressure signal; and
  a power control system operably coupled to the pressure source system, the power control system configured to determine, based at least in part on the pressure signal, an optimal hydraulic pressure oscillation frequency for a given procedure and output a control signal to the pressure source system, the power control system further configured to accept a user-defined peak pressure value to limit a peak pressure within the angioplasty balloon, the power control system further configured to monitor the pressure signal to detect fracture of the hardened material within the elastic conduit.

23. A system for applying a dynamic or static pressure to an angioplasty balloon comprising:
  a pressure source system configured to output at least a first pressure from a pressure source outlet;
  an angioplasty unit comprising an oscillating mechanism, an angioplasty balloon inflation device, and a balloon connector,
    wherein the oscillating mechanism comprises an input fluidly coupled to, and configured to receive at least the first pressure from, the pressure source outlet and an output fluidly coupled to the angioplasty balloon inflation device and balloon connector, and
    wherein the oscillating mechanism is configured to selectively actuate to output a plurality of pressure pulses and/or a static pressure;
  an angioplasty balloon catheter fluidly coupled to the balloon connector and comprising a pressure transducer, an elongated catheter, and the angioplasty balloon present at a distal end of the elongated catheter,
    wherein the elongated catheter is configured to deliver the plurality of pressure pulses or static pressure to the angioplasty balloon,
    wherein the angioplasty balloon is configured to receive the pressure pulses and/or static pressure, and
    wherein the pressure transducer is configured to measure fluid pressure within the angioplasty balloon catheter and output a pressure signal; and
  a control system operably coupled to at least one of the pressure source system, the angioplasty unit, and the angioplasty balloon catheter,
    wherein the control system is configured to adjust the actuation of the oscillating mechanism and/or pressure source outlet pressure.

24. The system according to claim 23, wherein the first pressure is a predetermined pressure.

25. The system according to claim 23, wherein the first pressure is ramped, stepped, oscillated, user guided, and/or pressure transducer feedback guided.

26. The system according to claim 23, wherein the oscillating mechanism and/or the angioplasty balloon inflation device are configured to provide static pressure to the angioplasty balloon.

27. The system according to claim 23, wherein the oscillating mechanism and/or the angioplasty balloon inflation device are selectively fluidly coupled to the angioplasty balloon catheter.

28. The system according to claim 23, wherein the control system is configured to adjust an actuation frequency and/or a duty cycle of the oscillating mechanism.

29. The system according to claim 23, wherein the control system is configured to determine optimal actuation settings of the oscillating mechanism and/or pressure source outlet pressure.

30. The system according to claim 29, wherein the control system is configured to adjust the actuation frequency of the oscillating mechanism and/or pressure source outlet pressure to previously determined optimal actuation settings.

31. The system according to claim 23, wherein the control system is configured to accept a user-defined peak pressure value to limit peak pressure within the angioplasty balloon.

32. The system according to claim 23, wherein the control system is configured to monitor the pressure signal to detect fracture of hardened material within an elastic conduit to which the angioplasty balloon is applied or system failure or leakage.

33. The system according to claim 23, wherein the angioplasty unit is configured to create pressure oscillations from zero or near zero pressure to at least a peak pressure at a frequency greater than or equal to an optimal hydraulic pressure oscillation frequency.

34. A system for applying a dynamic or static pressure to an angioplasty balloon comprising:
  a pressure source system configured to output at least a first pressure from a pressure source outlet;
  an angioplasty unit comprising an oscillating mechanism, an angioplasty balloon inflation device, and a balloon connector,
    wherein the oscillating mechanism comprises an input fluidly coupled to, and configured to receive at least the first pressure from, the pressure source outlet and an output fluidly coupled to the angioplasty balloon inflation device and balloon connector, and
    wherein the oscillating mechanism is configured to selectively actuate to output a plurality of pressure pulses and/or a static pressure; and
  an angioplasty balloon catheter fluidly coupled to the balloon connector and comprising a pressure transducer, an elongated catheter, and the angioplasty balloon present at a distal end of the elongated catheter, wherein the elongated catheter is configured to deliver the plurality of pressure pulses or static pressure to the angioplasty balloon, wherein the angioplasty balloon is configured to receive the pressure pulses and/or static pressure, and wherein the pressure transducer is configured to measure fluid pressure within the angioplasty balloon catheter and output a pressure signal, wherein the balloon connector and the elongated catheter are configured to reduce flow resistance of delivering pressure to the angioplasty balloon, and wherein pressure received by the oscillating mechanism from the pressure source outlet is a high pressure, comprising pressure of approximately 0-300 atm.

35. The system according to claim 34, wherein the elongated catheter is configured to receive a 0.014-inch guidewire.

36. A system for applying a dynamic or static pressure to an angioplasty balloon comprising:

a pressure source system configured to output at least a first pressure from a pressure source outlet;

an angioplasty unit comprising an oscillating mechanism, an angioplasty balloon inflation device, and a balloon connector, wherein the oscillating mechanism comprises an input fluidly coupled to, and configured to receive at least the first pressure from, the pressure source outlet and an output fluidly coupled to the angioplasty balloon inflation device and balloon connector, and wherein the oscillating mechanism is configured to selectively actuate to output a plurality of pressure pulses and/or a static pressure; and an angioplasty balloon catheter fluidly coupled to the balloon connector and comprising a pressure transducer, an elongated catheter, and the angioplasty balloon present at a distal end of the elongated catheter, wherein the elongated catheter is configured to deliver the plurality of pressure pulses or static pressure to the angioplasty balloon, wherein the angioplasty balloon is configured to receive the pressure pulses and/or static pressure, and wherein the pressure transducer is configured to measure fluid pressure within the angioplasty balloon catheter and output a pressure signal, wherein the pressure source system comprises a pressure-regulated high-pressure gas source, wherein the balloon connector and the elongated catheter are configured to reduce flow resistance of delivering pressure to the angioplasty balloon, and wherein the oscillating mechanism comprises a solenoid valve and deformable diaphragm system fluidly coupled to the pressure-regulated high-pressure gas source, the solenoid valve being configured to switch from a high-state to a low-state, in the high-state, a high-pressure gas from the gas source is connected to the deformable diaphragm that separates a gas side and a hydraulic side, in the low-state, the gas side is exhausted to atmospheric pressure, the solenoid valve selectively outputting at least a first pressure from the pressure source outlet.

37. The system according to claim 36, wherein the deformable diaphragm is a spring-loaded elastic diaphragm configured to accelerate depressurization of the angioplasty balloon.

38. The system according to claims 37, wherein the elongated catheter is configured to receive a 0.014-inch guidewire.

39. The system according to claims 36, wherein the elongated catheter is configured to receive a 0.014-inch guidewire.

* * * * *

UNITED STATES PATENT AND TRADEMARK OFFICE
CERTIFICATE OF CORRECTION

PATENT NO. : 11,464,949 B2
APPLICATION NO. : 16/654073
DATED : October 11, 2022
INVENTOR(S) : Robert Chisena et al.

It is certified that error appears in the above-identified patent and that said Letters Patent is hereby corrected as shown below:

In the Claims

At Column 22, Claim number 38, Line number 31, delete "claims" and insert -- claim --.

At Column 22, Claim number 39, Line number 34, delete "claims" and insert -- claim --.

Signed and Sealed this
Twenty-seventh Day of December, 2022

*Katherine Kelly Vidal*

Katherine Kelly Vidal
*Director of the United States Patent and Trademark Office*